United States Patent [19]
Maynard

[11] Patent Number: 5,405,337
[45] Date of Patent: Apr. 11, 1995

[54] SPATIALLY DISTRIBUTED SMA ACTUATOR FILM PROVIDING UNRESTRICTED MOVEMENT IN THREE DIMENSIONAL SPACE

[75] Inventor: Ronald S. Maynard, Sunnyvale, Calif.

[73] Assignee: The Board of Trustees of the Leland Stanford Junior University, Palo Alto, Calif.

[21] Appl. No.: 21,941

[22] Filed: Feb. 24, 1993

[51] Int. Cl.⁶ ............................................. A61M 37/00
[52] U.S. Cl. ........................................ 604/281; 604/95
[58] Field of Search .................. 604/95, 264, 280–284; 128/4, 772, 657, 658

[56] References Cited

U.S. PATENT DOCUMENTS

| | | | |
|---|---|---|---|
| 4,753,223 | 6/1988 | Bremer | 128/4 |
| 5,078,684 | 1/1992 | Yasuda | 604/281 |
| 5,229,211 | 7/1993 | Murayama et al. | 604/280 |
| 5,279,559 | 1/1994 | Barr | 604/281 |

OTHER PUBLICATIONS

Kuribayashi, Katsutoshi "Reversible SMA Actuator for Micron Sized Robot", Osaka Prefectural Industrial Research Institute, 1990.

Busch et al., "Prototype Micro-Valve Actuator", TiNi Alloy Company, 1990.

Ikuta et al., "Crystallographic Analysis of TiNi Shape Memory Alloy Thin Film for Micro Actuator", 1990.

Primary Examiner—John D. Yasko
Assistant Examiner—Manuel Mendez
Attorney, Agent, or Firm—Wilson, Sonsini, Goodrich & Rosati

[57] ABSTRACT

A flexible VLSI film containing shape memory alloy (SMA) actuator elements and associated control and driver circuitry is wrapped around any bendable element such as a flexible, hollow tube, catheter tube or the like. The SMA actuator elements are thus spatially distributed around the circumference of the bendable element. The SMA actuator elements are selectively resistively heated with an electric current through associated decode and driver circuitry, thereby causing a portion of the film to contract. The radical distribution of the SMA actuator elements across the surface of the VLSI actuator film is such that when properly activated, a device sheathed with the VLSI film is capable of executing highly dexterous maneuvers in three-dimensional space, which was not heretofore possible. The actuator elements are self-guided in that control circuitry, decode circuitry and associated microprocessors, including position mapping means are fabricated in VLSI integrally with the SMA actuator elements. Alternatively, a microprocessor controller may be located at a remote location while communicating with associated driver circuitry on the actuator film.

36 Claims, 12 Drawing Sheets

SPATIALLY DISTRIBUTED SMA ACTUATOR FILM PROVIDING UNRESTRICTED MOVEMENT IN THREE DIMENSIONAL SPACE

BACKGROUND

The field of the present invention relates generally to shape memory alloy (SMA) actuators. More particularly, the field of the present invention relates to a spatially distributed actuator film wherein a plurality of SMA actuator elements together with associated control and driver circuitry are deposited on a thin, flexible substrate using very large scale integrated circuit (VLSI) techniques.

The basis for a conventional steerable element such as a steerable catheter incorporating a shape memory alloy actuator is the ability of certain special alloys to undergo a micro-structural transformation from an austenitic phase at high temperature to a flexible, so-called martensitic phase at a lower temperature. One of the more common and useful alloys is a 49:51 composition of titanium and nickel (TiNi). The temperature at which the phase transition occurs is referred to as the activation temperature. For the foregoing composition, this is approximately 70° C. In the low temperature region, the SMA actuator is soft and exhibits a Young's modulus of 3,000 MPa. In this state, the shape memory alloy may be readily deformed up to 5% in any direction without adversely affecting its memory properties.

Once heated just beyond the activation temperature, a phase transformation from the soft, pliable martensite to harder, inflexible (6900 Mpa) austenite, the parent phase, takes place. That is, if the shape memory alloy material is not excessively deformed or is not over-constrained, it attempts to reorganize its structure to a previously "memorized" shape. If permitted to cool, the shape memory alloy becomes soft again and may be mechanically deformed to begin another cycle. The mechanical deflections produced by activating the memorized state can produce useful work if suitably configured. Although the recovery deflections may be small (5%), the recovery forces can range from in the neighborhood of 35 tons per square inch or more for linear contractions. Thus, the recoverable energy is considerable.

Any shape may be programmed into an SMA actuator element by physically constraining the piece while heating it to the proper annealing temperature. TiNi alloys are commercially available in sheet, tube and wire forms and can have a wide range of transformation temperatures.

A memory transformation of an SMA element is dependent upon temperature. However, the rate of deformation is dependent on the rate of cooling and heating. Therefore, the rate at which temperature changes take place dictates the maximum speed at which the SMA actuator can operate. As with all mechanical designs, there is a tradeoff. A faster actuating SMA actuator must be heated and cooled faster, thereby consuming more power and generating a larger amount of wasted heat.

It is known to use shape memory alloy actuators in conventionally steerable elements such as catheters. One such application, U.S. Pat. No. 4,543,090, describes a conventional steerable and aimable catheter using shape memory alloy as the control elements. Conventional steerable devices using SMA elements are severely limited in dexterity. Movement is limited to a single plane. Also, the SMA element must be mechanically deformed to begin another cycle.

Thus, in conventional applications, each shape memory element must be coupled to at least one other shape memory element. When one of the elements is heated, it is returned to its original position by the other memory element. This enables controlled motion, however only in a plane. The motion is limited to at most, two degrees of freedom per joint.

Conventional steerable devices such as catheters incorporating SMA actuators as control elements have considerable disadvantages. The joints must be made unduly large and cumbersome because an opposite force is always needed to return the SMA actuator element to its martensitic shape after transformation from the parent phase. Complex linkages are required in order to rotate such a steerable device. For example, the range of maneuverability is severely limited by the linkages which are necessary to return the SMA actuator element to its martensitic shape after it has been activated to assume its programmed shape.

Conventional steerable devices using shape memory alloys have a further disadvantage in that they are relatively large and have a severely constrained lower limit beyond which size reduction is not economically feasible. The relatively large size is due to the need for control arms, linkages or other elements which are necessary to return the shape memory actuator to its initial state. This severely constrains the geometry of such a conventional steerable device.

Conventional steerable devices incorporating shape memory alloys lack the dexterity and precise control necessary to maneuver into very small, geometrically complex spaces. This is due to the need for control arms or oppositely disposed elements for mechanically returning the actuator to a first position after it has been activated to its programmed state.

Conventional steerable devices using SMA actuators are often too slow for many medical applications where quick, dexterous movement is critical. The large size of conventional steerable devices using SMA elements requires an increased amount of current in order to produce the activation temperature needed for a quick transition from the martensitic state to the programmed or "memorized" austenitic phase. A conventional SMA actuator consumes a great deal of power, thus dissipating a large amount of heat. This necessarily slows down the cooling to the activation threshold and thereby slows down the transition from the austenitic state back to the martensitic state, resulting in a slower acting device.

What is needed is a steerable device which is capable of unrestricted yet highly precise and dexterous maneuvers in three-dimensional space. It would be advantageous to eliminate the need for control arms, linkages, or other extraneous means for returning conventional shape memory alloy elements to a first position after deactivation and the transition from the parent phase back to the martensitic state. Such control linkages increase the size of the device, increase power requirements and slow the dissipation of heat, resulting in a slow acting device.

What is also needed is a steerable device capable of unrestricted articulation in three dimensions, and which can be scalable for providing increased dexterity and maneuverability in very small, geometrically constrained areas which are presently inaccessible to conventional steerable devices.

SUMMARY

In order to overcome the above-discussed disadvantages of conventional steerable devices using shape memory alloy actuators, one aspect of the present invention utilizes the fact that SMA alloys can be deposited, patterned and annealed using conventional VLSI techniques. The broad range of fully developed VLSI tools and techniques greatly reduce the cost of fabrication and assembly of small steerable devices such as catheters. To fabricate a steerable device in accordance with the present invention such as a 6F (French) catheter, the SMA thin film actuators are deposited by conventional chemical vapor deposition (CVD), and VLSI techniques, and patterned on a thin, flexible silicon nitride or polyimide film. Electrical connections are made using standard photolithographic processes. After releasing the SMA actuator "skin" or film from its silicon processing base, it is adapted to be wrapped around any flexible surface to impart torque thereto, such as a force glove, or to impart three dimensional movement. In one embodiment, the SMA actuator film is adapted to be wrapped in a cylindrical configuration around a bendable element such as a flexible catheter tube, or the like. The SMA actuator elements are thereby spatially distributed around the circumference of the bendable element. The SMA actuator elements are then controllably selected to move the bendable element any direction in three-dimensional space.

The VLSI fabrication of the thin film SMA actuator elements in accordance with one aspect of the present invention achieves a more rapid dissipation of heat than is possible with conventional SMA devices. This results in a faster acting device. It also has the advantage that a steerable catheter sheathed with the SMA actuator film of the present invention can be articulated at 100 Hz. A catheter having a dimension of 6 French, encased by the SMA actuator film of the present invention, can be articulated at ½ second intervals.

In accordance with another aspect of the invention, a plurality of on-off switch means are integrally formed using VLSI techniques on the same flexible substrate which also forms the SMA actuator film. The switch means are disposed for providing a phase activation threshold current to selected SMA actuators to produce the phase transition from martensite to austenite and thereby impart desired movement. In a preferred embodiment, the switch means comprise a plurality of a CMOS power transistors. The transistors and associated address decode circuitry are operatively linked with a corresponding one of each of the SMA actuators for selectively applying a phase activation current thereto. VLSI fabrication eliminates the need for a multitude of current carrying wires to the SMA actuators. Only three leads, a ground lead, power lead., and data signal lead are necessary for linking address decode and circuitry with an external microprocessor. Alternatively, control data may be modulated along a single power lead.

A microprocessor controller is used for programming a predetermined path of travel for the SMA actuator film. The microprocessor is a separately packaged integrated circuit which communicates with the control circuitry on the SMA actuator film through conventional leads, or fiber optic links.

In accordance with another aspect of the present invention, the microprocessor includes a position mapping means. Pressure sensor means are disposed along the distal or active end of the SMA actuator film. The pressure sensor means provide output signals at precise positional intervals to the microprocessor. The output signals are representative of pressure sensed when the distal end or exterior skin of the SMA actuator film is pushed against a boundary defining a travel path such as the wall of an artery. The microprocessor, in accordance with well known adaptive feedback techniques, uses the output signals from the sensory means to determine a locus of angular positions for the SMA actuators which define an ideal path of travel as the SMA actuator film is advanced into a geometrically complex space. The position mapping means records the angular positions of the SMA actuators for precise positional intervals along the path of travel as the steerable device is advanced into a geometrically complex space. Upon retraction, the position mapping means produces output signals to the control circuitry for activating the SMA actuators in a reverse sequence along the path of travel. The configuration of the SMA actuator film is thereby automatically recreated for each of the positional intervals along its path of travel in a reverse direction. This enables the SMA actuator film of the present invention to maneuver dexterously in a reverse direction in geometrically complex spaces which are inaccessible to conventional steerable devices using SMA actuator elements.

In accordance with an aspect of the invention, the position of the distal or active end of the SMA actuator film can be inferred by measuring the resistance of the SMA actuator elements using conventional techniques which are well known to one skilled in the art. The resistance of each element is proportional to its temperature, thus to its activation state and to its angular position. Accordingly, the overall configuration of the SMA actuator film can be determined by the microprocessor for any given point in a locus of points which define a path of travel.

It will be appreciated that in accordance with another aspect of the invention, the SMA actuator film is self-guiding with respect to a locus of points defining an ideal path of travel, once the angular positions of the SMA actuator elements for each of those points have been stored in the position mapping means.

In accordance with another aspect of the invention, the reduced cost of the SMA actuator film made possible by VLSI fabrication enables the SMA actuator film to he detachable and disposable after use. The SMA actuator film which encases a catheter, for example, and enters an artery, is connected to external control circuitry over flexible leads through a simple plug/socket connector. The SMA actuator film is thereby detachable from control circuitry, and easily can be replaced after use.

The fabrication of the spatially distributed SMA actuators, associated address decode circuitry and power transistors using thin film VLSI techniques enables a steerable device in accordance with the present invention, to be capable of being scaled down in size to much less than 6F (French) which is equal to 1900 microns. This has many advantages over conventional steerable devices using SMA memory elements, including smaller size, greater maneuverability, lower power consumption, more rapid heat dissipation, and consequently, faster movement. The scaled down size achievable by the present invention also enables a device to dexterously maneuver through geometrically complex spaces in three dimensions which are inaccessible to conventional devices.

BRIEF DESCRIPTION OF THE DRAWINGS

These and other advantages of the present invention may be appreciated from studying the following detailed description of the invention together with the drawings in which.

DESCRIPTION

Overview

Figure 1A:
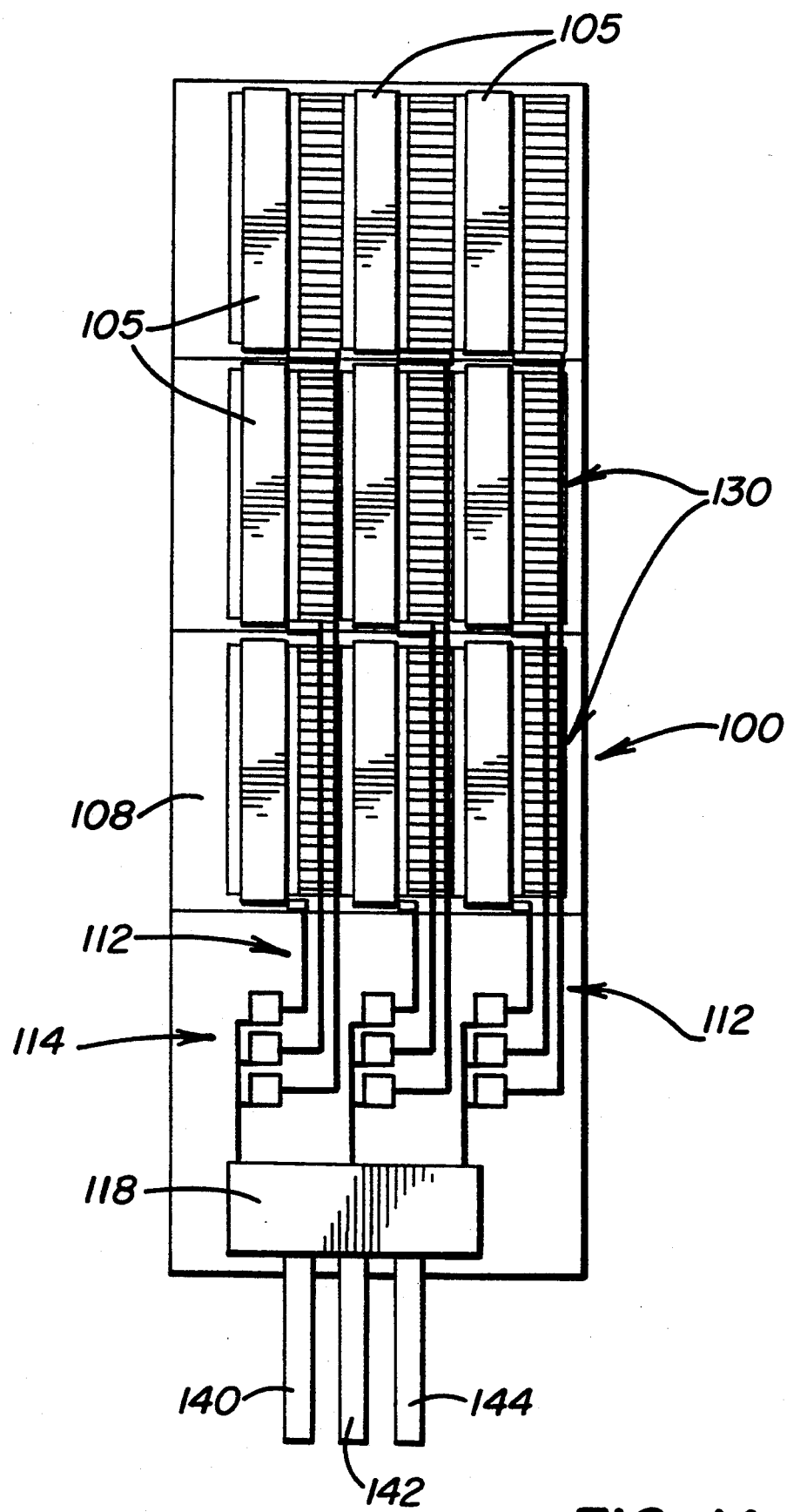
FIG. 1A is a top view of a first embodiment according to the present invention.
Figure 1B:
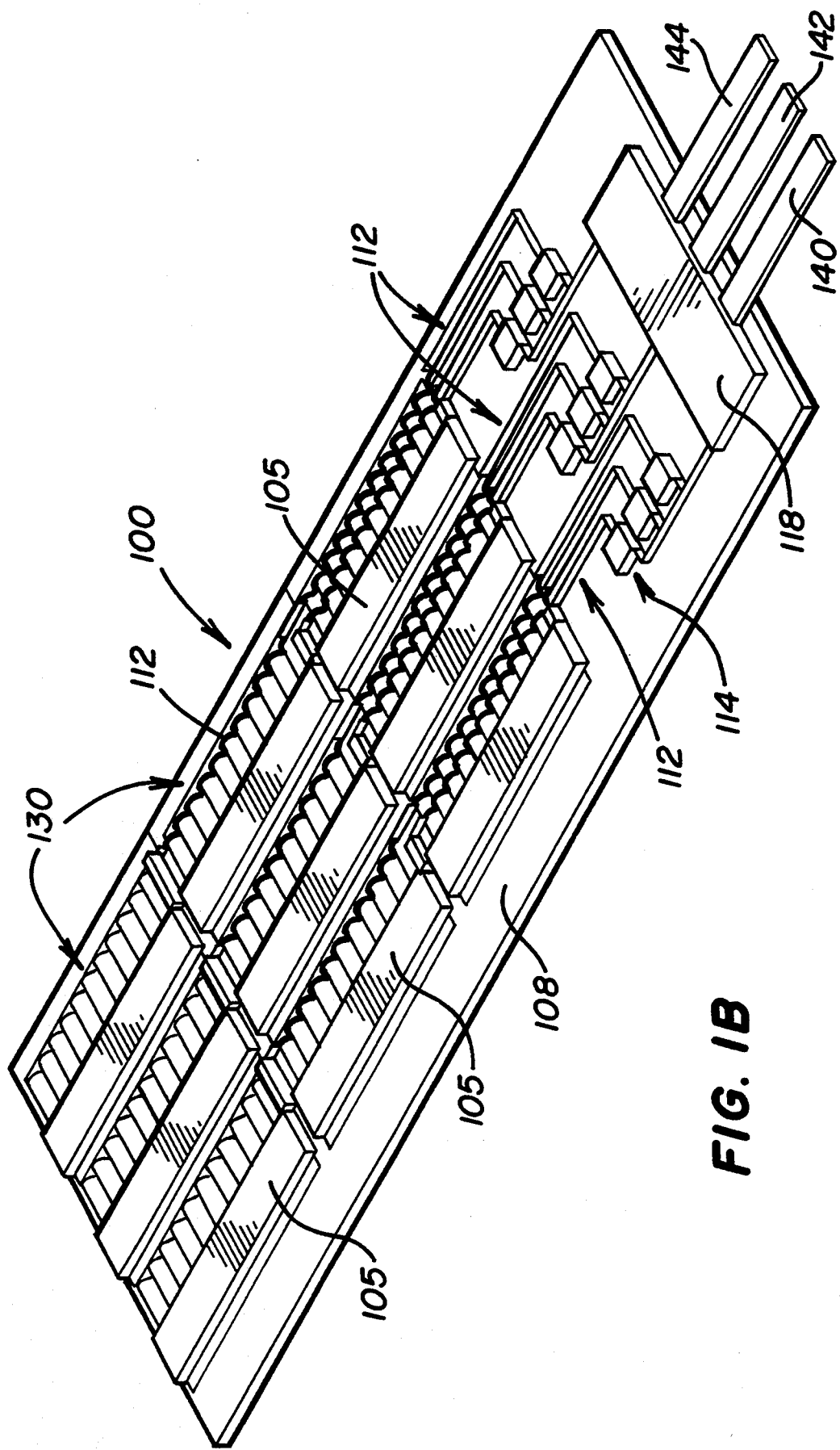
FIG. 1B is a perspective view of the embodiment depicted in FIG. 1A.
Figure 1C:
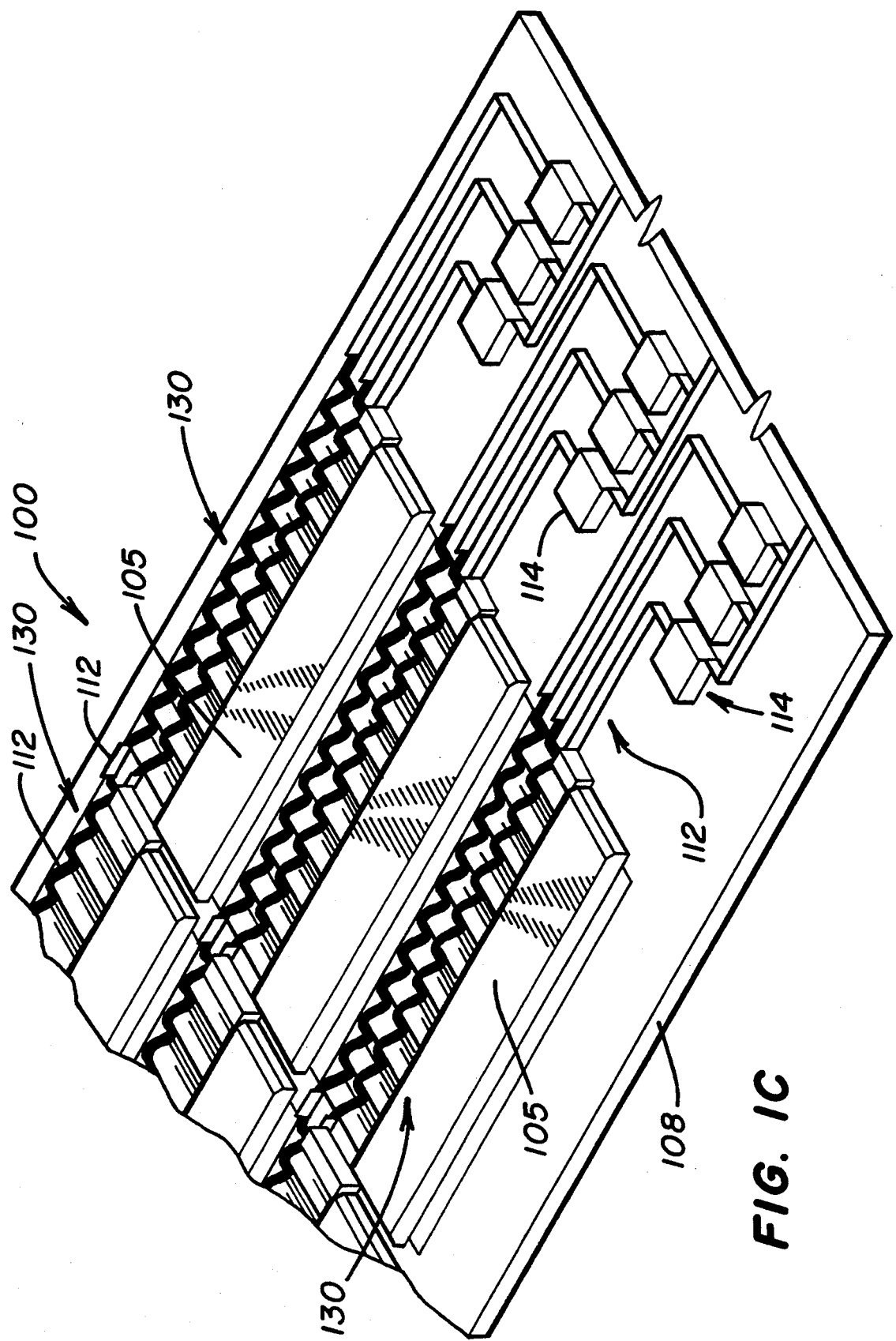
FIG. 1C is an enlarged perspective view of the embodiment depicted in FIG. 1A.

As shown in FIGS. 1A, 1B and 1C, a spatially distributed SMA actuator film 100 comprises a plurality of SMA thin film actuators 105 disposed in a distal portion thereof. The SMA actuators 105 are deposited, patterned and annealed on a layer of polyimide or kevlar based material using conventional VLSI techniques.

Electrical connections with address decode circuitry 118 and associated switch means 114 such as CMOS transistors are made using standard VLSI photolithographic processes.

The layer 108 of polyimide or kevlar based material is released from a silicon processing base using standard techniques such as EDH each, or the like. This subsequently forms a self-contained, flexible SMA actuator film 100 wherein the SMA actuators 105, as well as associated switch means 114 for applying the phase activation current to selected SMA actuators 105, and address decode circuitry 118 are integrated in VLSI on a compact, flexible SMA film 100.

Figure 3A:
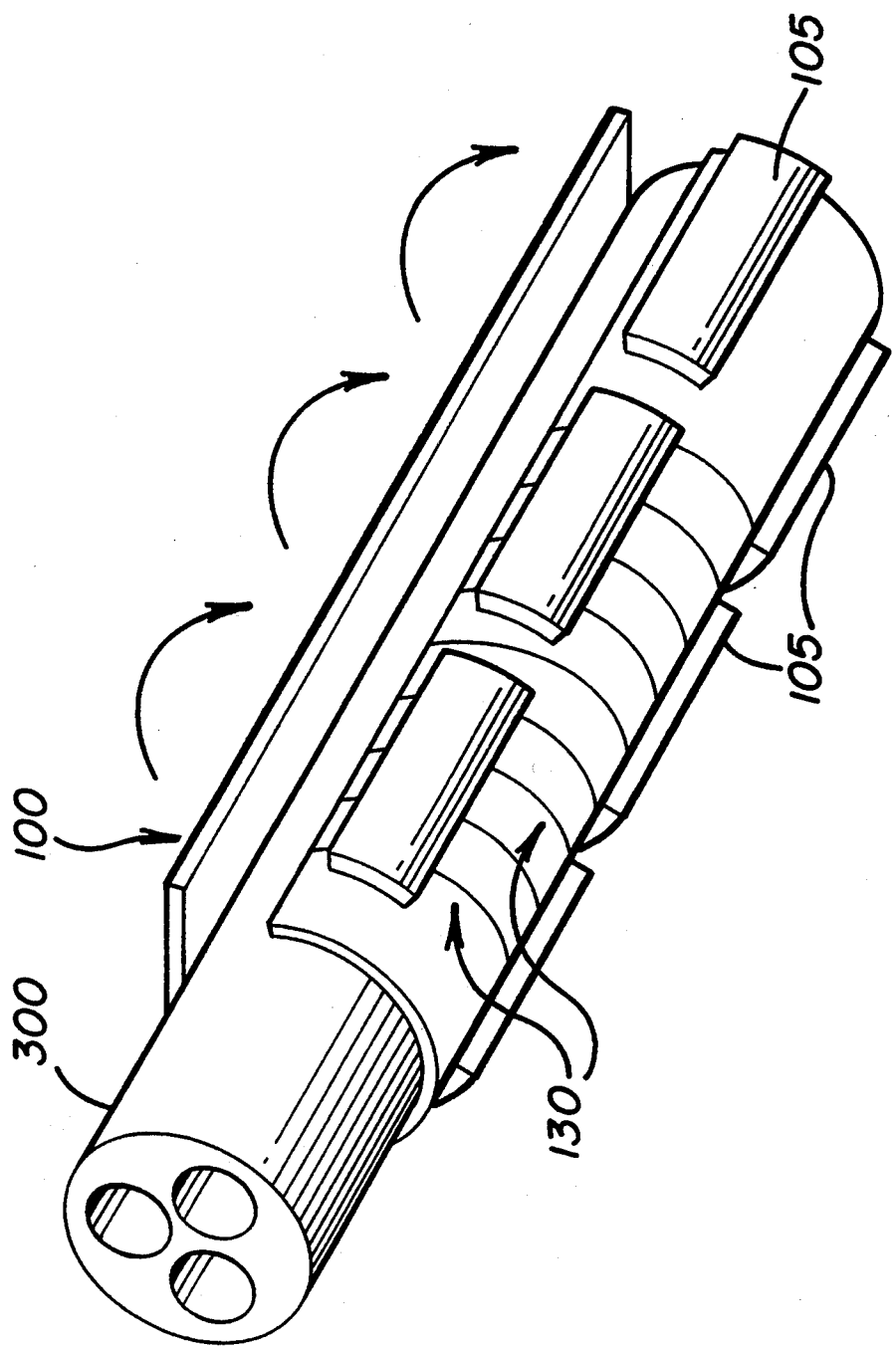
FIG. 3A is a cut-away perspective view of the embodiment depicted in FIG. 1 showing how the spatially distributed SMA actuator film of FIG. 1 is adopted to be wrapped around and secured to a flexible, bendable structure.
Figure 3B:
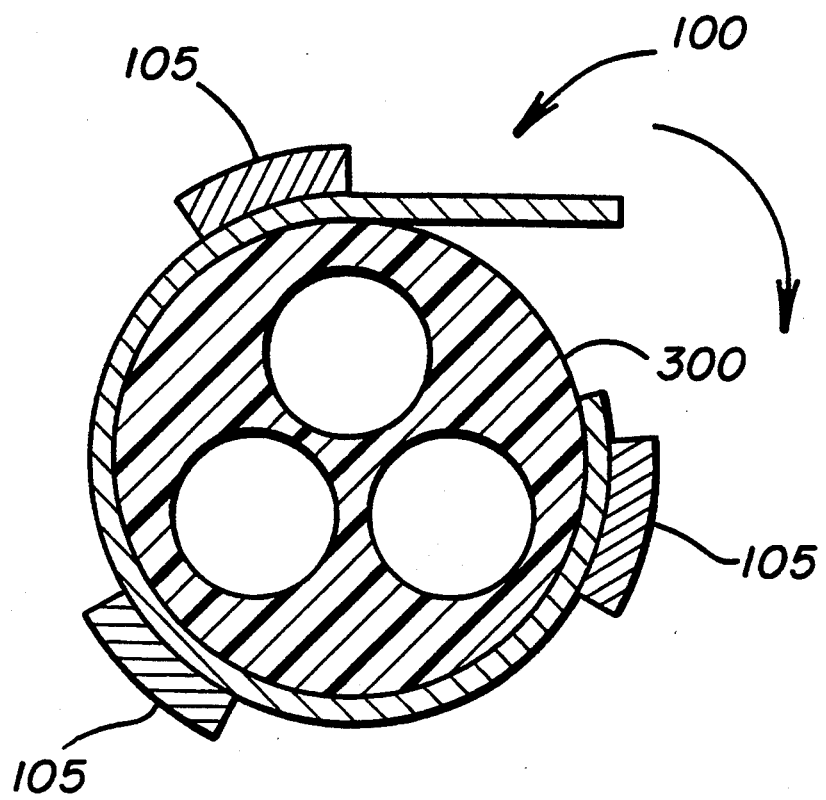
FIG. 3B is a side sectional view of the embodiment depicted in FIG. 3A.

The SMA actuator film 100 is adapted to be wrapped around any surface configuration to impart torque thereto, such as a force glove or the like. In a preferred embodiment, the SMA actuator film 100 is adapted to be wrapped around a bendable element such as a catheter tube 300, or the like as shown in FIGS. 3A and 3B. Accordingly, a plurality of SMA actuators 105 are then evenly distributed around the surface of the SMA actuator film 100 which encases the bendable element 150. Selective activation of the SMA actuators 105 by the control circuitry thereby imparts continuous movement in any direction in three dimensional space to the bendable element.

In the example shown in FIG. 3B, three thin film SMA actuators 105 are positioned at 120° intervals around a flexible catheter tube 300. With reference to FIG. 1, the SMA actuators 105 are selectively addressed by address decode circuitry 118 and are resistively heated by transistor switch means 114 to a phase activation threshold in accordance with techniques which are well known. Selectively applying a current to one or more of the SMA actuators 105 which is sufficient to activate the shape memory phase transition produces a differential contraction on one side of the tube 300, and local bending.

The SMA actuators 105 are deactivated by removing the current source thereby permitting heat to flow from the SMA actuator 105. The rate at which the SMA actuators cool is determined by their thickness. It will be appreciated that the spatially distributed SMA actuators 105 form a multijointed manipulator or multi-segmented probe which is not constrained to move in a single plane but can bend in any direction with unrestricted motion.

It also will be appreciated that the integration of the SMA actuators 105 in overlapping arrays in a flexible VLSI film produces a continuity of moveable SMA nodes which are spatially distributed around the circumference of a bendable element. This enables a bendable element encased by the SMA actuator film 100 of the present invention to be capable of substantially continuous movement in three dimensions along its length. Thus, the SMA actuator film 100, when wrapped around a catheter tube or the like, is able to execute extremely dexterous maneuvers in three-dimensional space. This was not possible with conventional steerable devices using shape memory alloy actuators which are constrained to move in a single plane.

Process for Making the SMA Actuator Film

Figure 2A:
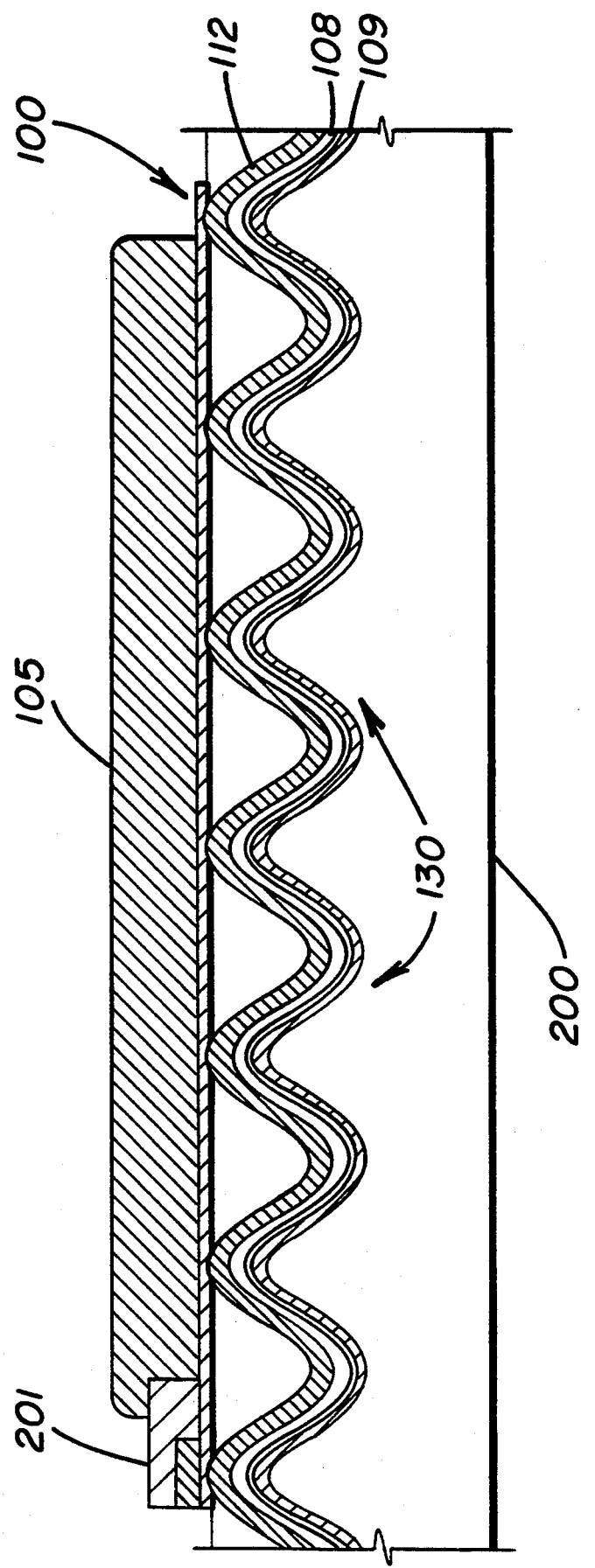
FIG. 2A is a side sectional view of the embodiment depicted in FIG. 1A.

Referring now to FIGS. 1C and 2A, in accordance with one aspect of the invention, the overall process for forming the spatially distributed SMA actuator film is as follows:

A substrate 200 is initially provided as a foundation for VLSI integration of control and address circuitry and SMA actuator elements. A standard silicon wafer, [100]Si, having a thickness of approximately 500 microns is a suitable base substrate material.

Next, a series of grooves are formed in the silicon wafer using an anisotropic etch. The grooves provide a corrugated foundation in substrate 200 which will be used to form a series of corrugations 130 in a subsequently deposited polyimide layer 108 which will be used to form the VLSI SMA actuator film 100.

The corrugations 130 are located substantially beneath each SMA actuator element 105. The corrugations are disposed substantially transversely to the axes of deformation or actuation axis of the SMA actuator elements 105. The corrugations 130 provide a means for enabling the actuator elements 105 to deform upon actuation and to impart movement to an entire adjacent portion of SMA actuator film 100. The corrugations 130 thus facilitate the controlled movement of the SMA actuator film 100 upon application of an electric current. The size and configuration of the corrugations 130 can be scaled to maximize the movement induced in the SMA actuator film 100 by the contraction or expansion of actuator elements 105.

The corrugations 130 also provide a means for limiting strain in the actuator elements and in the SMA actuator film 100 and thus prevent breakage of the SMA actuator film 100. In a preferred embodiment, the corrugations 130 limit the strain to approximately ≦8%.

After the forming the corrugations 130, a thin insulating layer 109 of SiNi is deposited over the wafer 200 using conventional VLSI techniques which are well-known. The layer 109 of SiNi acts as an oxygen barrier to prevent contamination of the TiNi layer which is to be sputtered in a subsequent process step. The layer 109 of SiNi has a thickness which is on the order of 2000 Å.

The shape memory alloy material such as a 50:50 or 49:51 TiNi formulation is then sputtered over the layer 109 of SiNi in accordance with well-known CVD/VLSI techniques. The TiNi is then annealed to its programmed parent phase. The annealing process is dependent upon the formulation of TiNi used. The TiNi layer is typically annealed at 510° C.–540° C. for one hour.

As will be explained, the TiNi layer 105 can be annealed to optimize the useful torque to be extracted from the transition to the parent phase. The layer of TiNi is then patterned and etched according to known VLSI techniques to form discrete TiNi SMA actuators 105. The TiNi actuators 105 are then masked.

A layer 108 of polyimide or other kevlar based material is deposited over the TiNi actuators such that windows are formed around each TiNi actuator. The layer 108 of polyimide provides the foundation for the VLSI fabrication of switch means 114, address decode circuitry 118 and conductive paths 112 as shown in FIG. 1B. The polyimide layer 108 can be as thin as one-half micron.

Polyimide has proved to be a high precision, high strength mechanical material, which is especially applicable in this case when SMA actuators and associated control and driver circuitry must be integrated in VLSI on a very thin sheet which must exhibit great flexibility, yet be high in strength.

While polyimide is preferred as a foundational material, the VLSI SMA actuator film is not intended to be limited to polyimide and any appropriate flexible sheet material for accepting VLSI processing techniques may be implemented without departing from the scope of the invention.

A plurality of switch means 114 such as CMOS transistors suitable for VLSI fabrication are provided over the polyimide layer 108. Each switch means 114 is connected by conductive paths 112 to a corresponding SMA actuator 105 for applying a high current to that actuator to quickly resistively heat the SMA actuator to its activation threshold. Each switch means 114 is in turn connected with address decode circuitry 118 which is also fabricated using conventional VLSI techniques on the polyimide film 108. In a preferred embodiment address decode circuitry 118 comprises a series of latch registers, logic gates, or the like which are easily fabricated in VLSI.

Conductive paths 112 between each of the TiNi actuators and associated switch means and address decode circuitry are also fabricated using conventional VLSI techniques at this time.

As shown in FIG. 2A, a conductive lead 112 makes electrical contact with one end of an SMA actuator 105 through conductor termination block 201. A ground plane (not shown) is provided in the polyimide layer 108 to provide a return current path for the SMA actuators 105 in accordance with well known techniques.

VLSI sensor means such as capacitive linear strain gauges, Hall effect sensors, temperature sensors, or the like are likewise integrated in VLSI on the polyimide layer 108 and are associated with a corresponding SMA actuator or segment of SMA actuator film 100 as will be explained.

The polyimide layer 108 is then released from its silicon wafer processing base 200 by using a conventional etching process such as an EDP etch. It will be appreciated that the polyimide sheet now comprises a fully integrated VLSI shape memory alloy actuator film 100. That is, the SMA actuators 105, address decode 118 and control circuitry, including switch means 114, as well as positional sensors and sensors for measuring environmental parameters, are all integrally formed as a VLSI circuit incorporated in a flexible polyimide sheet 100.

The fully integrated VLSI SMA actuator film 100 is detachably connected to a power source through power lead 142. The SMA actuator elements are connected to a common ground through ground lead 140.

A microprocessor (not shown) can be integrated in VLSI on a proximal portion of the polyimide sheet 100 with address decode circuitry 118. Alternatively, a microprocessor can be provided as a separately packaged integrated circuit and operatively connected with the address decode and control circuitry on the polyimide sheet 100 through data lead 142.

The foregoing process provides a self-contained, fully integrated VLSI SMA actuator film 100 which can be operated in either open loop or closed loop mode to provide unrestricted motion in three dimensions as will be explained.

As shown in FIGS. 1A, 1B, and 1C in accordance with another aspect of the invention, the self contained VLSI SMA actuator film 100 may be viewed as a module. The data signal lead 144, power lead 142 and ground lead 140 are adapted to connect together a plurality of cascaded VLSI SMA actuators 100 as modules. The VLSI SMA modules are combined in sequential fashion. The data signal lead 144, power lead 142 and ground lead 140 of a first VLSI SMA actuator film module are carried forward to the address decode circuitry 118 of each successive VLSI SMA actuator module. Thus, a plurality of VLSI shape memory actuator modules may be cascaded together for certain applications.

The Shape Memory Actuators

In a preferred embodiment, the SMA material is a 49:51 composition of titanium and nickel (TiNi). The SMA material is available from RAYCHEM Corporation, 300 Constitution Drive, Menlo Park, Calif. 94025. The SMA actuators 105 are highly thermally sensitive elements which are resistively heated to a phase activation threshold temperature upon the application of a small electric current through leads 112 as shown in FIG. 1.

The formation of the SMA actuators is done according to VLSI techniques which are well-known. Typically, a suitable matrix of shape memory material such as TiNi is vaporized using ion bombardment in a low-pressure chamber. The vaporized shape memory alloy atoms travel to a substrate, in this case the silicon nitride base layer 109, where the atoms condense in a film. Referring to FIG. 1, the shape memory actuator film is patterned to form an array of SMA actuator elements 105 by conventional VLSI photolithography and etching operations to remove the sputtered SMA material from areas where it is not desired. Thus, a plurality of SMA actuator elements 105 are left on top of the silicon nitride layer 109 as shown in FIGS. 1 and 2.

The SMA actuator film is annealed at high temperature in accordance with known techniques. The annealing process programs the predetermined shape into the SMA actuator elements which the elements will assume after the microstructural transformation from the martensitic phase to the parent or austenitic phase. Any shape may be programmed into the alloy by physically constraining the piece while heating it to the proper annealing temperature. For 49:51 TiNi, that temperature is approximately 510° C. for one hour. This is known as the aging treatment.

In a preferred embodiment, a 49:51 TiNi alloy is utilized for a one-way shape memory actuator. During the aging treatment, the sputtered SMA film is constrained in what is intended to be the high temperature shape. It will be appreciated that any type of shape for maximizing the amount of movement from the low temperature or martensitic phase to the high temperature or austenitic phase may be programmed. In the aging treatment, a precipitation reaction in a TiNi alloy occurs. It is believed that the precipitate particles effectively create a back-stress which causes a deflection away from the constrained shape (in the austenitic or programmed phase) when the SMA actuator element is released and cooled. Upon cooling, the TiNi alloy will spontaneously deflect away from its constrained or programmed shape.

It is known that the activation temperature for the phase transformation from martensite to austenite is alloy dependent and can be altered by changing alloy composition. In accordance with another aspect of the invention, this enables the phase activation temperature to be optimized to determine the minimum threshold current which is necessary to achieve the spontaneous change of phase to the programmed shape.

A phase transformation from martensite to the parent phase or austenite is solely dependent on temperature. However, the rate of deformation is dependent on the rate of cooling and heating. Therefore, the rate at which temperature changes takes place dictates the maximum speed at which a SMA actuator can operate. As with all mechanical designs there is a tradeoff. A faster actuating SMA actuator must be heated and cooled faster, thereby consuming more power and generating a larger amount of waste heat.

As the SMA actuator elements 105 are selectively resistively heated by the application of an electric current, they generate controlled movement of an adjacent portion of SMA actuator film 100. A 49:51 titanium nickel (TiNi) shape memory alloy is the preferred material because this exhibits a large change in shear modulus over a relatively narrow temperature range. The change in modulus at the activation temperature is the result of a reversible martensite to austenite solid state phase transformation.

One aspect of the present invention provides significant power savings over conventional SMA devices. The alloy mixture is optimized at 49:51 TiNi such that a minimum threshold current is applied to the actuator elements 105 to achieve a maximum amount of useful movement during the transition from the martensitic phase to the austenitic phase.

With regard to the configuration of the SMA actuator elements, the TiNi or other suitable shape memory alloy is sputtered so as form a matrix of atoms which provide a pulling force by contracting when transformed to the high temperature austenitic phase. This shape may be set by sputtering a matrix of suitable TiNi material in a compressed configuration so that the SMA actuator element is programmed upon annealing to be in a close, compacted configuration. This is the so called parent phase, the shape which is "remembered" at elevated temperature. This is also termed the austenitic phase. Thus, at a temperature below the activation temperature, the TiNi elements can be flexed outward and extended. Upon application of an electric current, which resistively heats the SMA actuator element to the phase activation temperature, the SMA actuator element spontaneously assumes its programmed configuration and contracts the entire adjacent actuator film.

This is analogous to sputtering the SMA actuator material in a configuration which may be likened to a compression spring in its "remembered" or programmed phase. Such a configuration would spontaneously contract to provide a pulling force when the SMA actuator element is resistively heated to the phase activation temperature. Thus, such a configuration would provide a pulling force when activated. Whether the SMA actuator film of the present invention operates in the compression or tensile mode depends upon the mechanical constraints which are imposed on the elements after annealing.

Various configurations of the SMA actuator elements may be patterned by VLSI techniques to optimize the pushing or pulling force which occurs during the phase transformation from martensite to austenite. In the preferred embodiment, the SMA actuators contract upon being resistively heated to the activation threshold.

In summary, the SMA actuator material is deposited, patterned and annealed using conventional VLSI techniques. The associated switch means 114 and address decode circuitry 118 are also deposited in VLSI on the polyimide layer. The polyimide layer 108 is released from its silicon processing base in accordance with conventional etching techniques which are well known. This provides a flexible, modular SMA actuator film 100 wherein the SMA actuators 105, associated control circuitry, such as switch means 114 and address decode circuitry 118 are all integrated together in VLSI on the same flexible substrate.

It will be appreciated that the flexible SMA actuator film 100 may be configured around any surface to impart movement or torque thereto. When the SMA actuator film is wrapped around a central longitudinal axis, the spatial distribution of the SMA actuator elements 105 around the circumference of the SMA actuator film 100 provides multi-node articulation in three dimensions. A multi-jointed probe according to one aspect of the present invention is capable of performing highly dexterous maneuvers in three-dimensional space without restriction.

One aspect of the invention overcomes a significant problem with conventional SMA steerable devices. This problem concerns the critical restraints placed on the size and number of current carrying conductors.

Large TiNi actuators draw a great deal of current requiring a corresponding increase in the cross sectional area of the conductors. This is not compatible with devices having tight dimensional constraints. The foregoing poses a critical problem which, until now, has not been overcome. For example, some conventional TiNi actuated catheters can only support a single moveable joint due to this limitation.

To make a conventional SMA actuated steerable catheter work with precision, it would be necessary to deliver approximately 3 amps to the TiNi actuator. The space constraints placed upon current supplying feed wires are such that larger devices draw a great deal of current if the TiNi actuators are directly heated. The current supplying wires would have to be prohibitively large and would inhibit movement of the device.

Another problem with conventional SMA steerable devices is that TiNi is difficult to control accurately, since TiNi exhibits a temperature versus resistance relationship with a significant hysterisis curve.

Figure 2B:
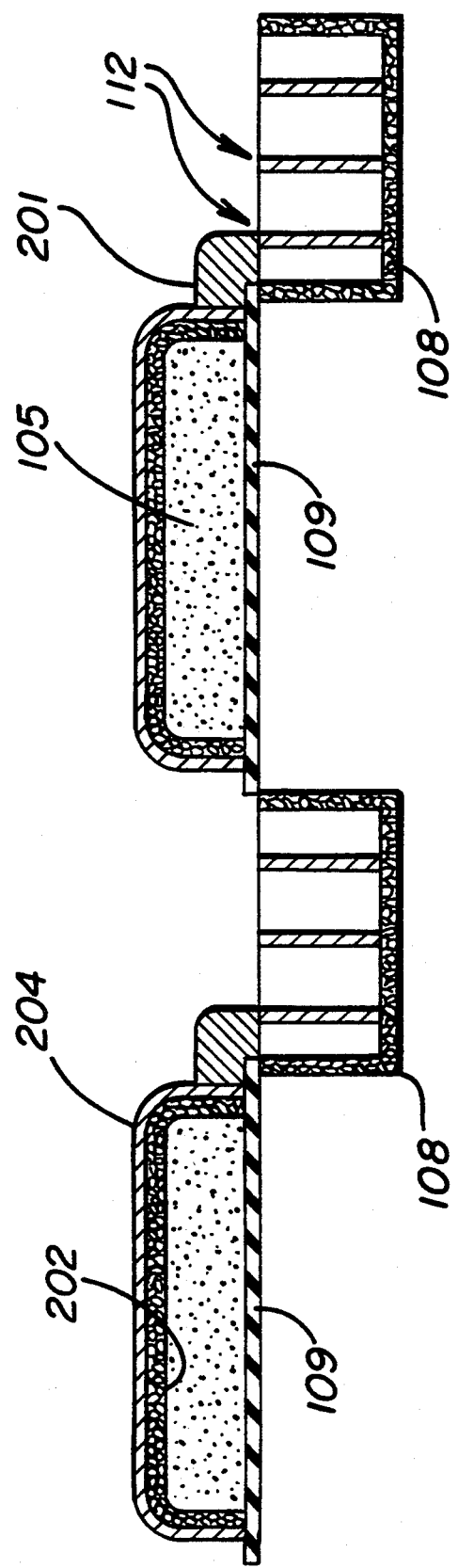
FIG. 2B is a sectional end view of an alternate embodiment of the invention shown in FIG. 1A.

In order to overcome the foregoing disadvantages of conventional SMA/TiNi actuated devices, one aspect of the invention, as shown in FIG. 2B, provides a thin layer strain relief 202 of flexible, insulating material such as polyimide which is deposited over each TiNi actuator 105. The strain relief layer 202 has a thickness on the order of 20,000 Å. Strain relief layer 202 can be thicker or thinner, depending on the overall dimensions of the SMA actuators. Subsequently, a very thin conductive layer 204 is provided adjacent the stress relief or insulating layer 202. The thin conductive layer 204 comprises an ohmic heating means for providing a high resistance heat source to the TiNi actuator 105. The conductive layer 204 is also termed an ohmic heating layer and preferably comprises a thin layer of approximately 50:50 nickel chromium (NiCr).

The NiCr ohmic heating layer 204 provides a higher resistance than bulk TiNi and ohmically heats the TiNi element 105 to its phase activation threshold by thermal conduction through insulating layer 202. The TiNi element 105 is not electrically connected to ohmic heating layer 204.

It has been found that the use of an ohmic heating layer 204 in the present invention achieves a considerable advantage over known SMA actuators in that the supply current is greatly reduced, by at least two orders of magnitude, for the same power delivery. This is especially advantageous for devices of larger dimensions, where supply current is critical. For example, in a large dimensional SMA steerable device without the ohmic heating layer 204, the supply current would have to be increased to an almost prohibitive degree in order to achieve useful movement.

It has been found-that an ohmic heating layer 204 comprising a metal such as NiCr does not exhibit the resistance versus temperature hysterisis curve of TiNi and is therefore capable of being controlled with great accuracy. The ohmic heating layer 204 comprising NiCr is characterized by a linear resistance versus temperature behavior, unlike TiNi, thereby considerably reducing the controlling effort.

In accordance with this aspect of the invention, the linear temperature versus resistance response of the ohmic heating layer 204 is used to infer the temperature of an associated SMA actuator 105 and thus the degree of actuation and position of the associated SMA actuator 105.

A predetermined current is passed through the ohmic heating layer 204. Circuit means are provided in accordance with known VLSI techniques for measuring the drop in potential across the electrical connections for ohmic heating layer 204. This thereby enables the resistance of the ohmic heating layer 204 to be determined.

Since the ohmic heating layer 204 is characterized by a linear resistance versus temperature response, the temperature of the ohmic heating layer 204 is readily determined from the known resistance. The temperature of ohmic heating layer 204 is substantially equal to that of the associated SMA/TiNi element. Thus, the temperature indicates the degree of actuation or activation state of the associated SMA actuator 105, and consequently the position of the associated SMA actuator. From this, the SMA actuators can be precisely controlled in accordance with conventional techniques which are well known.

Referring now to FIGS. 3A and 3B, in accordance with one aspect of the invention, the flexible substrate comprising the SMA actuator film 100 is adapted to be configured around a central longitudinal axis to provide unrestricted motion in three dimensions. The SMA actuator film 100 is wrapped around a bendable element such as hollow, flexible catheter tube 300 or the like. It will be appreciated that the corrugations 130 allow maximum movement of the SMA actuator elements 105 and consequently maximize the bending of the cylindrically configured SMA actuator film 100 in any direction in three-dimensional space. The interleaved arrays of SMA actuator elements 105, when wrapped around the circumference of bendable element 300, as shown in FIG. 3B, facilitate unrestricted movement of the SMA actuator film 100 in three-dimensional space. As set forth previously, the corrugations 130 also advantageously provide a useful means for limiting the strain of the SMA actuator film 100 as it moves along a complex path. This has the advantage of enabling strain to be increased to approximately 8%, far greater than that of conventional SMA actuator devices.

In the example of FIG. 3B, the interleaving of the SMA actuator elements 105 is such that for a given segment of the SMA actuator film 100, three SMA actuator elements are disposed approximately 120° apart from one another around the circumference at bendable element 300. However, any convenient arrangement of SMA actuator elements around the circumference of bendable element 200 is possible, for example, four SMA elements disposed at 90° intervals.

In accordance with an aspect of the invention, the size and configuration of the SMA actuator elements 105 may be selected so as to optimize the torque requirements for moving the underlying bendable element 300. For example, the TiNi material may be sputtered to assume a form analogous to a compression spring in its activation phase.

The recovery forces of the SMA elements 105 which move bendable element 300 with unrestricted movement in three-dimensional space are substantial. The recovery forces achieved during the phase change from martensite to austenite are in a range of from 35 to 60 tons per square inch. Thus, in accordance with one aspect of the invention, the SMA elements may be scaled down in size to provide considerable force at very small dimensions.

Overall Operation

The basic operating principle of a VLSI shape memory alloy actuator device in accordance with an aspect of the present invention is straightforward. A flexible VLSI film comprising a plurality of SMA actuators 105 and associated address decode 118 and driver circuitry 114 is adapted to be wrapped around a bendable element. Accordingly, a plurality of thin film SMA actuators are positioned at regular intervals around a bendable element such as a flexible catheter tube or the like. Selectively applying an electric current to one or more of the SMA actuators 105 produces a differential contraction on one side of the tube 300, producing local bending.

Referring again to FIGS. 1 and 2, the SMA actuator elements 105 comprise thermally activated means for generating controlled movement. Each SMA actuator element 105 is connected with a corresponding switch means 114 for applying a suitable electric current capable of resistively heating each selected SMA element to its predetermined phase activation temperature. The switch means 114 comprise CMOS power transistors which likewise are formed on the silicon substrate 200 using VLSI techniques which are well known. The switch means 114 also can be either MOSFET or bipolar power transistors.

Each CMOS power transistor 114 is operatively connected through leads 112 with an address decoding circuit means 118 for selectively enabling one or more CMOS power transistors, as shown in FIG. 1. The address decode circuit means 118 is provided with a ground lead, power lead and data enable lead as shown in FIG. 1. Address decode circuit means 118 is likewise formed using VLSI techniques which are well-known. Alternatively, address decode circuit 118 may be a separately packaged integrated circuit.

Address decode circuit means 118 comprises a series of logic gates or latch registers or other convenient means for selectively addressing each SMA actuator element 105 in response to signals from a microprocessor.

A microprocessor is connected with address decode circuit means 118 over the data signal lead. The microprocessor determines which SMA actuators or group of SMA actuators 105 are to be activated so as to achieve the desired movement of the SMA actuator film 100. In accordance with techniques which are well known, the microprocessor loads a selected activation pattern into the latch registers of address decode circuit means 118. The address decoding circuit means 118 then selectively enables CMOS power transistors 114. The enabled CMOS power transistors 114 then apply a current of predetermined activation threshold to corresponding SMA actuator elements 105. This effects the phase transformation of the selected SMA actuators to thereby execute a desired maneuver in three-dimensional space as determined by the microprocessor. It is preferable to locate a resistive heating means such as thin film, series resistor (not shown) as close as possible to each SMA actuary 105. This advantageously increases the rate of resistive heating; resulting in a faster acting device.

Figure 5:
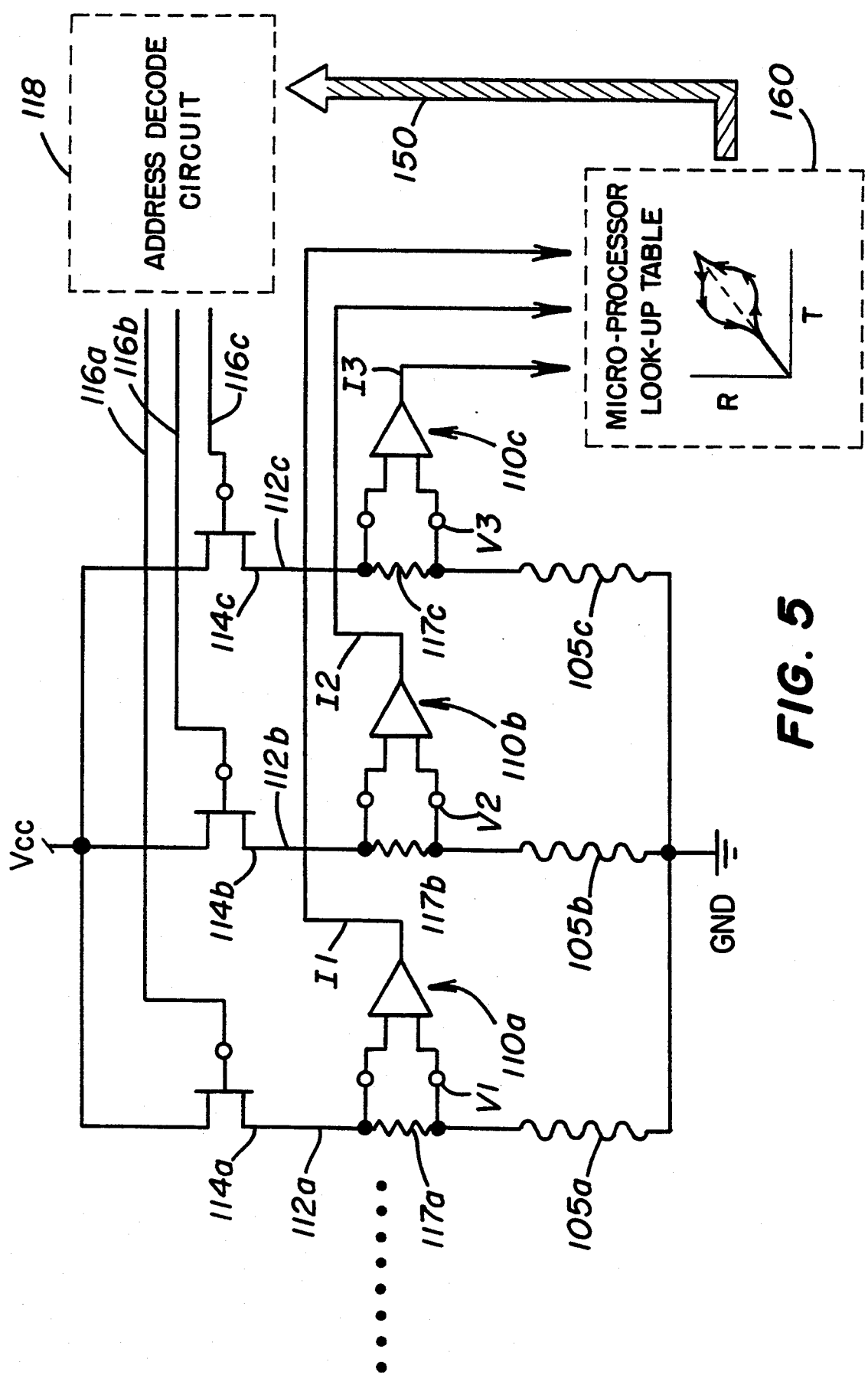
FIG. 5 is an equivalent circuit diagram of the embodiment depicted in FIG. 1.

The microprocessor may be located remotely from the actuator film 100 as shown in FIG. 5. This is advantageous when large memory capacity is required, as for example when mapping the path of travel of the actuator film 100 as it is advanced into a geometrically complex space. Remote location of the microprocessor controller also is advantageous when extreme down-sizing, for example to a few microns in diameter, of the actuator film probe is required for medical applications. This enables the probe to be down-sized while maintaining a large memory capacity at a remote location.

A bendable element, such as a catheter tube, encased by the SMA actuator film is not constrained to move in a single plane, but can bend in any direction. Thus, the present invention, for the first time, provides a spatially distributed SMA actuator film which achieves unrestricted motion in three-dimensional space. The spatially distributed actuator film of the present invention can produce almost a continuous path of motion throughout a bendable element which it encases due to the overlapping of the interleaved arrays of actuator elements 105 as they are wrapped around a bendable element. These and other aforementioned features of the invention produce highly dexterous movements in three-dimensional space.

Figure 4:
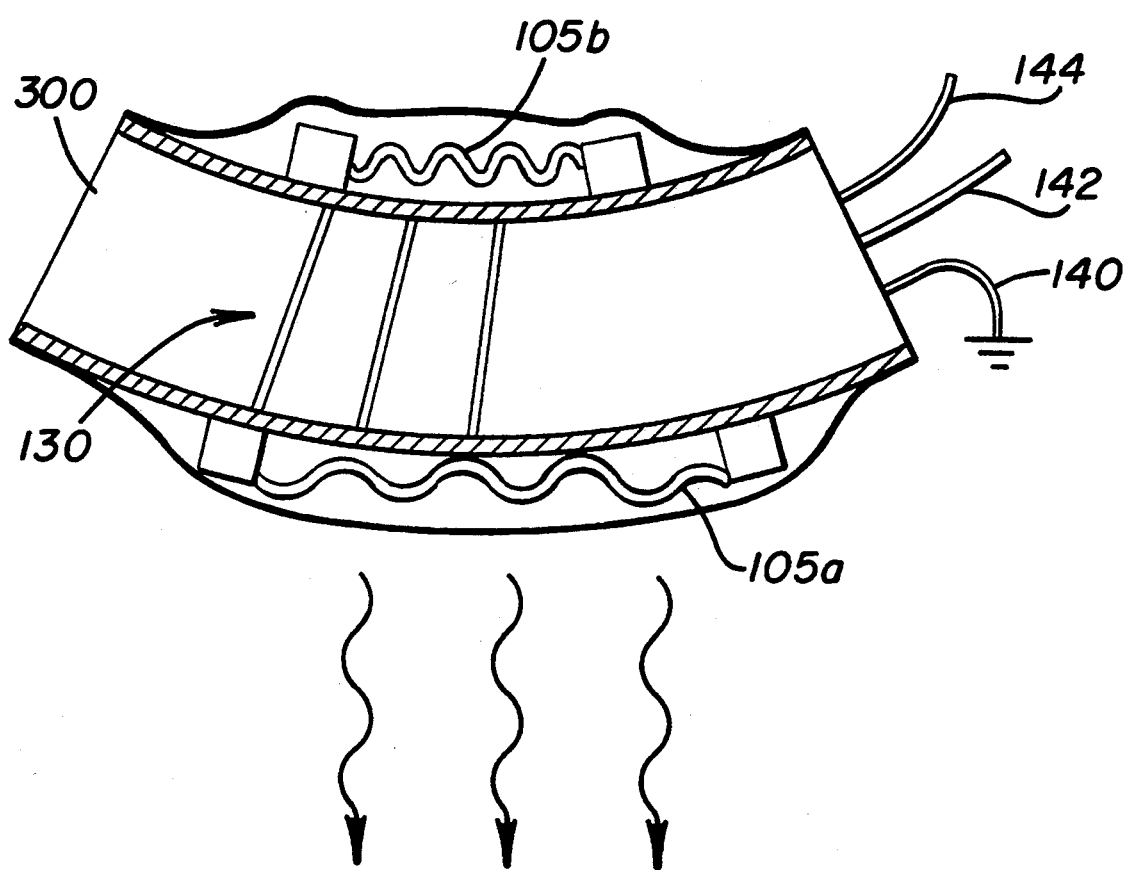
FIG. 4 is a perspective, sectional view of the embodiment depicted in FIGS. 3A and 3B, showing the phase activation action of an SMA element.

In the example shown in FIG. 4, SMA actuator element 105a is selected and resistively heated. The arrows shown indicate the dissipation of heat from the actuator element. The corrugations 130 allow congruent expansion and contraction of opposite sides of the bendable element 300. In FIG. 4, the contracted configuration of actuator element 105b is the programmed shape or parent phase which actuator element 105b spontaneously assumes once the phase activation temperature is reached.

It will be appreciated that the phase transition to martensite from austenite is crystallographically reversible upon cooling. The inherent resiliency of the flexible polyimide forming the foundation for the SMA actuator film returns the SMA activator elements 105 to their pliable martensite shape upon deactivation. Thus, no opposing force is needed to return a deactivated SMA actuator element to its flexible or martensitic state. This has a further advantage in that the rate of movement of the SMA actuator film 100 can be closely controlled by the microprocessor. For example, the rate of movement can be increased by minimizing the activation time during which an electric current is applied to resistively heat each SMA actuator element, thus increasing heat dissipation and a reversible martensitic phase transformation as soon as the temperature of the SMA actuator element falls below the activation threshold. The selective time dependent activation of the SMA actuator elements is done in accordance with microprocessor control techniques which are well known.

Activation of SMA Actuators

FIG. 5 shows an equivalent circuit for the device of FIG. 1. In this example, SMA actuators 105a, 105b, 105c are adapted to be spaced at 120° intervals around the circumference of SMA actuator film 100 when it is wrapped around a bendable element as shown in FIGS. 3A and 3B. It is understood that a plurality of SMA actuators 105 overlap in the direction parallel to the central axis of the SMA actuator film 100 as shown in FIG. 1 to provide a substantially continuous range of motion. For the sake of clarity, the circuit of FIG. 5 shows only one row or segment of the SMA actuator film. A plurality of SMA actuators 105 are controlled by the circuit of FIG. 5.

It will also be appreciated by those skilled in this art that the SMA actuator film 100 of the present invention is not limited to a cylindrical configuration. Rather, the SMA actuator film could be adapted to any surface configuration such as a glove or the like to provide force feedback. The following description of control circuitry is valid for all such alternative configurations.

Referring again to FIG. 5, SMA actuators 105a, 105b, 105c have a common ground. A plurality of switch means 114a, 114b, 114c are connected to a corresponding SMA actuator element 105a, 105b, 105c through an associated power lead 112a, 112b, 112c. The transistors may be CMOS, MOSFET, or bipolar power transistors 114a, 114b, 114c which function as switch means for applying an activation threshold current to each corresponding SMA actuator 105a, 105b, 105c. Any switch means adapted for applying a threshold activation current and suitable for implementation in VLSI may be used. In a preferred embodiment, switch means 114 comprise CMOS power transistors.

There are many possible equivalent connection schemes for activating the SMA actuator elements 105. In a preferred embodiment, each transistor switch means 114a, 114b, 114c, has its drain connected to a corresponding SMA actuator element 105a, 105b, 105c, etc., and its source coupled to a power source Vcc. The gates of the CMOS power transistors 114a, 114b, 114c are coupled to address decode circuitry 118 through respective data lines 116a 116b, 116c.

In response to signals from the microprocessor communicated over the data signal lead 150, the address decode circuitry 118 sends an enable signal over data lines 116a, 116b, 116c to the gates of one or more selected CMOS transistors 114a, 114b, 114c. When the gate of a selected CMOS transistor switch means, for example, 114a, is enabled, transistor 114a produces a high output current on its drain or output lead 112a which is connected with a corresponding SMA actuator element 105a. Preferably, the output current from the CMOS power transistors 114 is optimized to the phase activation threshold of the corresponding SMA actuator element 105. Upon activation, the selected SMA actuator elements 105 undergo the substantially instantaneous phase change from martensite to austenite, thereby imparting useful movement to an adjacent segment of flexible SMA actuator film 100. The selected SMA actuators 105 are activated as long as it is necessary to hold the probe in a desired configuration.

The SMA actuators 105 are deactivated simply by removing the current source, thereby permitting heat to be dissipated. The rate at which heat dissipates to below the activation threshold determines the speed of the device. The flexible SMA actuator film 100 in which the SMA actuator elements 105 are disposed has sufficient resiliency to return the SMA actuators 105 to their original position substantially instantaneously when the temperature goes below the activation threshold.

For smaller devices, heat dissipates faster from the SMA actuators 105 and advantageously can result in an extremely fast acting device. For example, a device in accordance with the present invention at 6 French, can be articulated in three dimensions at one-half second intervals. The present invention achieves faster articulation because the SMA actuator elements contract as a function of impedance. Smaller SMA actuator elements have less impedance and at the same time dissipate heat more quickly.

For larger dimensions, the SMA actuator elements 105 in accordance with the present invention receive an activation current applied through a resistive heating means such as a thin ohmic heating layer of NiCr disposed over a thin strain relief layer of polyimide or the like adjacent the SMA element 105 as shown in FIG. 2B. The enable current from the output lead of a selected CMOS power transistor 114 then is applied to the corresponding input end of the resistive heating means for quickly heating the selected SMA actuator element 105 to an activation threshold.

Figure 6:
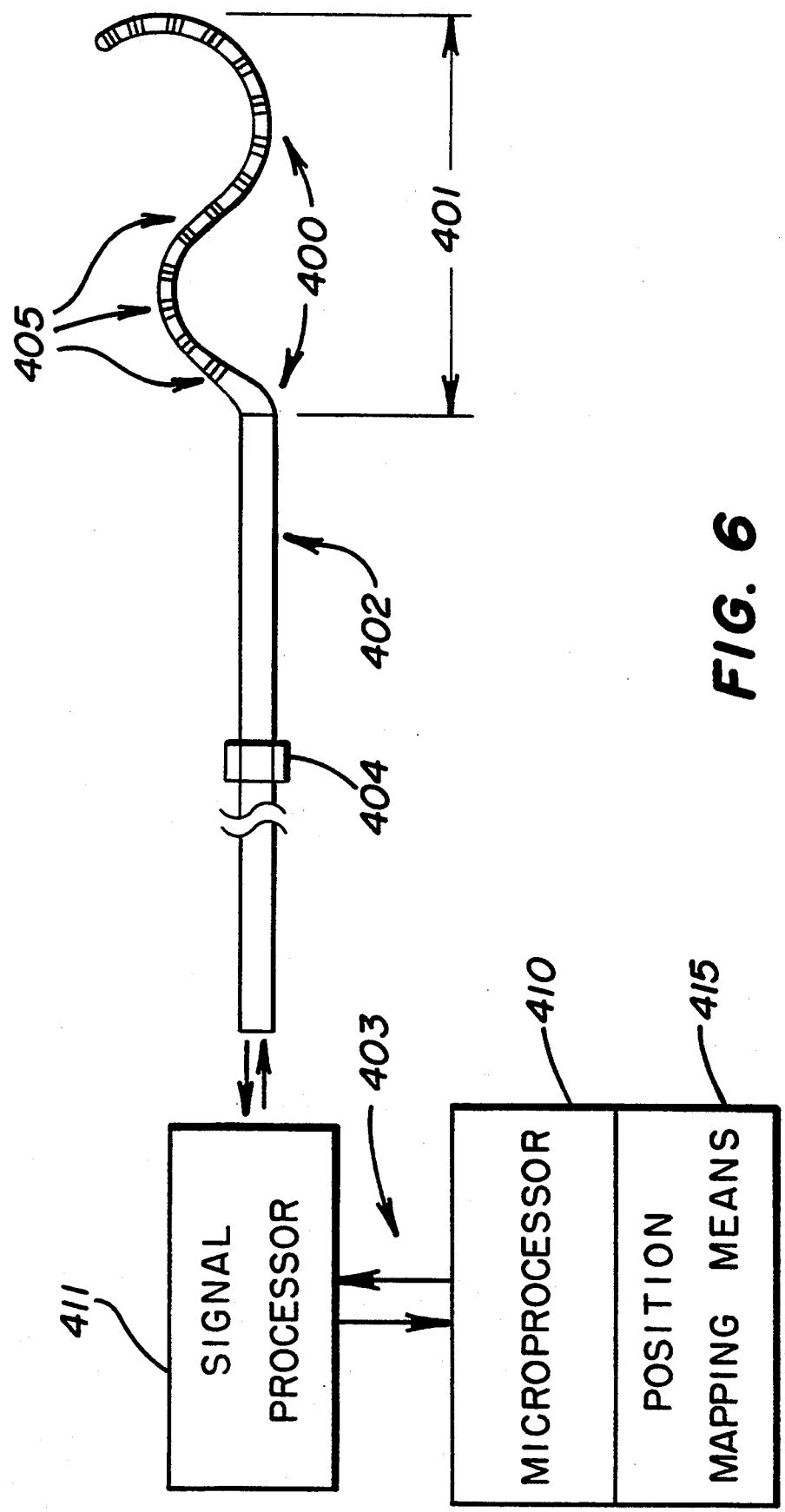
FIG. 6 is a perspective view of an embodiment according to the present invention showing an example of distributed articulation in three-dimensional space.

Referring now to FIG. 6, in accordance with another aspect of the present invention, a spatially distributed SMA actuator film 100 as previously described is wrapped in a cylindrical configuration to form a flexible multijointed manipulator or probe 400 capable of performing highly dexterous maneuvers in three-dimensional space. In the example shown, the probe 400 includes a distal portion 401 comprising the flexible VLSI SMA actuator 401 film which is, for example, 5 centimeters long. This is the maneuverable or active portion of the probe 400 which is provided with the spatially distributed array of SMA actuator elements. It is understood that the distal portion 401 can be made longer than 5 cm in order to access a geometrically complex space.

In FIG. 6, a microprocessor 410 is operatively connected to the proximal end 402 of probe 400. As is readily understood by those skilled in the art, the probe 400 comprises the VLSI shape memory actuator film 100 shown in FIG. 1 which is wrapped in a cylindrical configuration to form a probe 400 capable of multi node articulation in three dimensions. As previously explained, the SMA actuators are spatially distributed around the circumference of the distal portion 401 of probe 400 to provide unrestricted, highly dexterous maneuvers in three dimensional space. It is understood that the address decode and control circuitry such as the transistor switch means of FIG. 1 are integrated in VLSI in a proximal portion 402 of probe 400. The foregoing SMA actuators and control circuitry are omitted from FIG. 6 for the sake of clarity.

In the embodiment shown in FIG. 6, the microprocessor 410 communicates through conventional leads or fiber optic leads 403, through a signal processing means 411, with the transistor switch means and address decode circuitry (as shown in FIG. 1) which are disposed on the proximal end 402 of the probe 400. A conventional fiber optic coupler (not shown) is provided for coupling the fiber optic signals to the driver circuitry in accordance with techniques which are well-known. The microprocessor 410 includes a position mapping means 415 for recording and storing a locus of angular positions for the SMA actuators representative of an axis of travel for the distal portion 401 of probe 400 as it is advanced along a travel path.

The probe 400 is detachable from the microprocessor at coupling 404. Coupling 404 is a simple plug/socket connector. Alternatively, coupling 404 may be any convenient means for detachably coupling the communication leads 403 from the probe 400. Since the probe 400 is fabricated using VLSI techniques, it is cost effective to make the probe 400 detachable and disposable after use. This has an advantage in medical applications of obviating the need for time consuming and complex sterilization procedures.

Operation of Control System

The invention can be operated in either open loop or closed loop mode. In open loop mode, a predetermined path of travel is programmed in the microprocessor 410. The microprocessor then provides output signals to the address decode circuitry which is integrated in VLSI on the proximal portion 402 of the probe 400 as previously explained. The predetermined travel path is then mapped into the latch registers or logic gates in the address decode circuitry in accordance with techniques which are well known. The address decode circuitry then activates selected SMA actuators disposed in the distal portion 401 of probe 400 to move the probe in accordance with the programmed travel path as previously explained.

The invention also can operate in a closed loop mode. In the closed loop mode, this aspect of the invention uses adaptive feedback control methods to center the probe 400 on a path of travel. Referring to FIG. 5, the microprocessor is able to determine the angular displacement and thus the position of each of the TiNi elements which comprise SMA actuators 105a, 105b, 105c and so forth. From this, the overall position and configuration of the SMA actuator film or probe easily can be determined for given positional intervals.

Angular displacement of the SMA elements 105 is determined by sensing the voltage drop across a low value resistor 117a, 117b, 117c. Each resistor 117a, 117b, 117c is fabricated in VLSI in accordance with known techniques and is connected with a corresponding SMA actuator 105a, 105b, 105c and so forth. Conventional means are provided for sensing the voltages at nodes V1, V2, V3 and so forth. The voltage information is provided to a microprocessor over a communication path in accordance with techniques which are well known.

Current sensor means 110a, 110b, 110c and so forth are also connected for measuring current delivered to each corresponding SMA actuator 105a, 105b, 105c, etc. The current sensor means comprise differential amplifiers 110a, 110b 110c for measuring current delivered to each corresponding SMA actuator. Current values for each SMA actuator 105a, 105b, 105c are sensed at the output leads I1, I2, I3 of each respective differential amplifier 110a, 110b, 110c, respectively. The output leads I1, I2, I3 are provided to a microprocessor over a communication path.

The SMA actuator elements are current driven devices. The actuation temperature which effects a phase transformation of the SMA actuators 105a, 105b, 105c and so on, is an intrinsic property of the alloy. For a 50:50 percent mixture of TiNi, the actuation temperature is a constant 70° C. For a 49:51 composition of TiNi in a preferred embodiment, the actuation temperature is a constant 100° C. It will be appreciated that by sensing the voltages at nodes V1, V2 and V3 and current at I1, I2, I3 for precise positional intervals along a path of travel, the resistance of each respective element and consequently its angular displacement for each positional interval along a path of travel easily can be determined by the microprocessor. Since the phase transition temperature of the actuator elements is constant, the resistance of each SMA element has a direct relationship with its angular displacement.

A look-up table 160 of temperature/resistance relationships is embodied in the microprocessor in accordance with techniques which are well known. Since there is a constant current source for each and every CMOS transistor 114a, 114b, 114c, sensing the voltages at nodes V1, V2 and V3, and current at I1, I2, I3 gives a measure of resistance for each corresponding SMA actuator element 105a, 105b and 105c.

The look-up table 160 is optimized for each TiNi formulation of the SMA actuators in order to provide a narrow hysterisis loop in accordance with techniques which are well known. In the look-up table, the microprocessor then correlates each resistance value with a temperature and consequently can determine the activation state and thus, the angular displacement and position of each of the SMA elements 105a, 105b and 105c at a given positional interval. The locus of angular positions for each SMA actuators defines the overall configuration of the probe 400 for each interval. From this, the overall configuration of the probe can be determined for any point along a path of travel.

In accordance with techniques which are well known, a position mapping means 415 in the microprocessor (shown in FIG. 6) comprises a means for establishing a reference array comprising a locus of angular positions for the SMA actuators. This in turn defines a path of travel for the probe 400. Once a locus of angular positions for the SMA actuator elements is stored, the memorized travel path is repeatable with extreme speed. Accordingly, a probe 400 or a catheter, or the like, encased by the SMA actuator film according to the present invention can instantly reverse both its direction and activation sequence so that it precisely retraces even the most complex path of travel. In this sense, a probe 400 incorporating the SMA actuator film of the present invention is self-guiding with respect to even the most complex path of travel, once it is stored in the position mapping means.

It will be appreciated that the position mapping means 415 may store one or more paths of travel in memory. This has the advantage of enabling the probe 400 according to the present invention to precisely repeat a selected path of travel and thereby be self-guided once the path of travel has been stored in the position mapping means. This has numerous applications in robotic surgery and in non-destructive testing or like application where it is advantageous to precisely configure a multijointed manipulator to conform to a predetermined path of travel.

In accordance with another aspect of the invention, a plurality of pressure sensor means 405 are provided along the exterior of the distal portion 401 of the SMA actuator film 100 as shown in FIG. 6. The pressure sensor means are used for adaptive feedback control of the probe 400. In this aspect of the invention, the goal of the adaptive feedback control is to minimize sensed pressure everywhere on the exterior or outer skin of the distal portion of probe 400. Known feedback methods are then used to center the probe on a path of travel.

Figure 7:
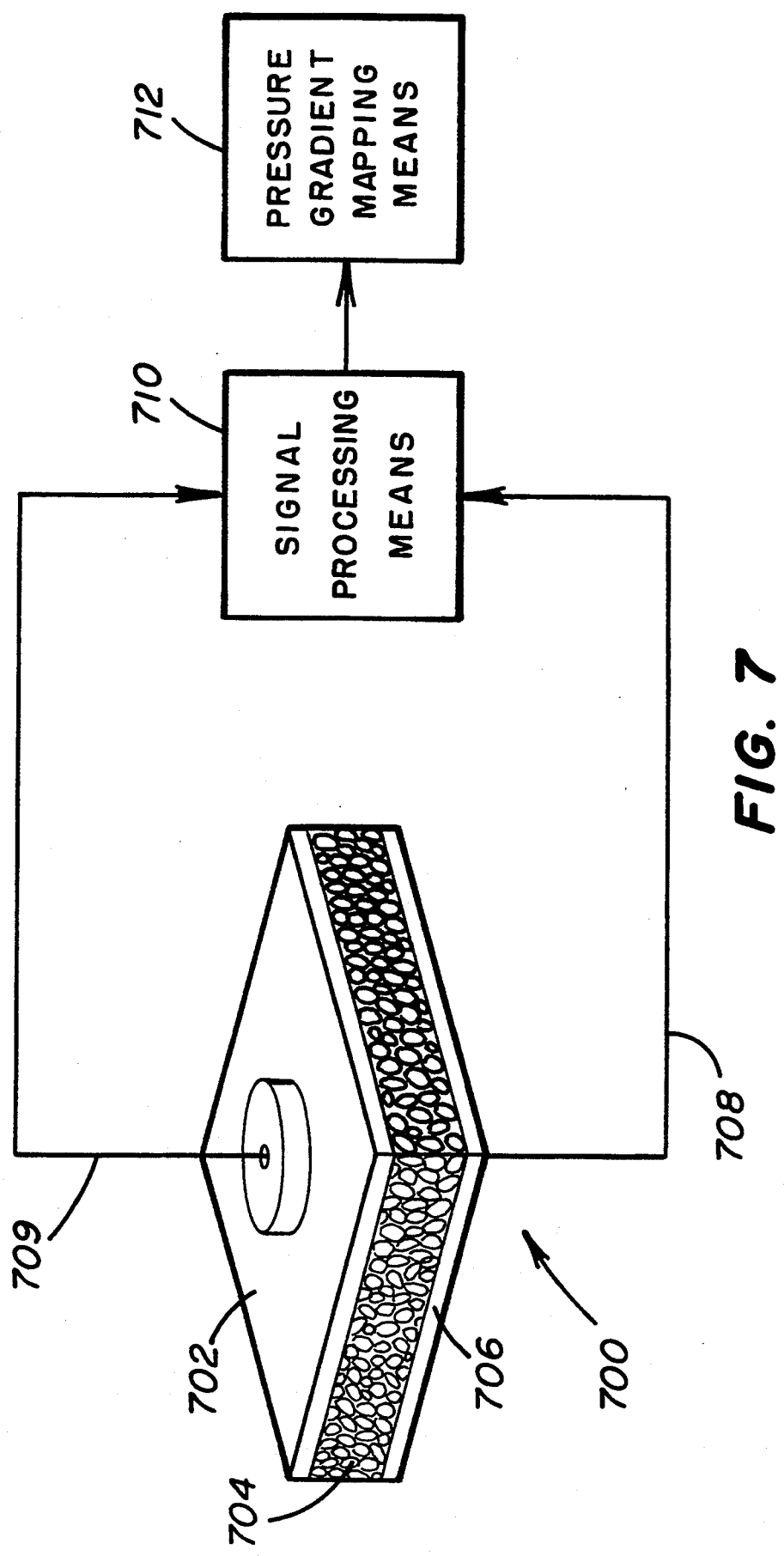
FIG. 7 is a schematic diagram of a typical pressure sensor means for adaptive feedback control of the embodiment shown in FIG.

FIG. 7 shows a representative capacitive pressure sensor means 700 for sensing very small changes in pressure as a function of capacitance. Pressure sensor means 700 comprises two opposed nickel or chromium nickel (CrNi) plates 702, 706 which are sputtered or deposited in accordance with well known VLSI techniques to encase a polyimide interlayer 704. The polyimide interlayer 704 is also formed by conventional VLSI techniques. It will be appreciated that the pressure sensing means 700 is adapted to be integrally formed as part of the VLSI process which forms the SMA actuator film 100 as previously described. The pressure sensor means 700 is adapted to be incorporated over or substantially adjacent a suitably configured TiNi element or SMA actuator 105. However, the pressure sensor means 700 also could be incorporated at any convenient location in the exterior portion of the actuator film 100 as shown in FIG. 6.

In operation, a voltage source is provided on lead 708 of the pressure sensor means 700. The dimensions of the pressure sensor 700 and voltage values on lead 708 are optimized in accordance with techniques which are well known such that even a slight pressure against the thin film plate 702 produces a measurable increase in capacitance. Since the signals representative of the change in capacitance produced on output lead 709 are very weak, a signal processing means 710 is provided locally for preprocessing the signals from pressure sensor 700 before sending the signals on to a pressure gradient mapping means 712 in the microprocessor. Because the signals from pressure sensor 700 are small, the signal processing means eliminates those signals which are above and below a predetermined threshold. The signal processing means 710 is also preferably provided close to the pressure sensor means 700 in order to eliminate noise.

The signal processing means 710 provides signals representative of small changes in capacitance to the pressure gradient mapping means 712. The pressure sensor 700 is calibrated such that a signal representative of an increase in capacitance is used to infer a predetermined amount of pressure. The signal processing means 710 provides a plurality of representative relative pressure readings back to the pressure gradient mapping means 712.

The pressure gradient mapping means 712 makes a pressure gradient map for a locus of positions defining a path of travel for the probe. As set forth previously, adaptive feedback means are provided for centering the probe on a path of travel which minimizes overall pressure for every point on the probe. The pressure gradient mapping means 712 determines which areas of the probe need to have pressure alleviated and in what direction. In accordance with techniques which are well known, a look-up table (not shown) of capacitance/pressure values is incorporated in the microprocessor. The microprocessor uses the look-up table to determine the actuation sequence of the SMA actuator elements in order to minimize pressure in a selected zone of the probe.

In accordance with another aspect of the invention, precise control of the SMA actuator film is achieved by a plurality of thin film capacitive linear strain gauges which are integrated in VLSI in the SMA actuator film accordance with techniques which are well known. Each capacitive linear strain gauge is disposed for measuring the angular displacement of a corresponding SMA actuator 105.

Figure 8:
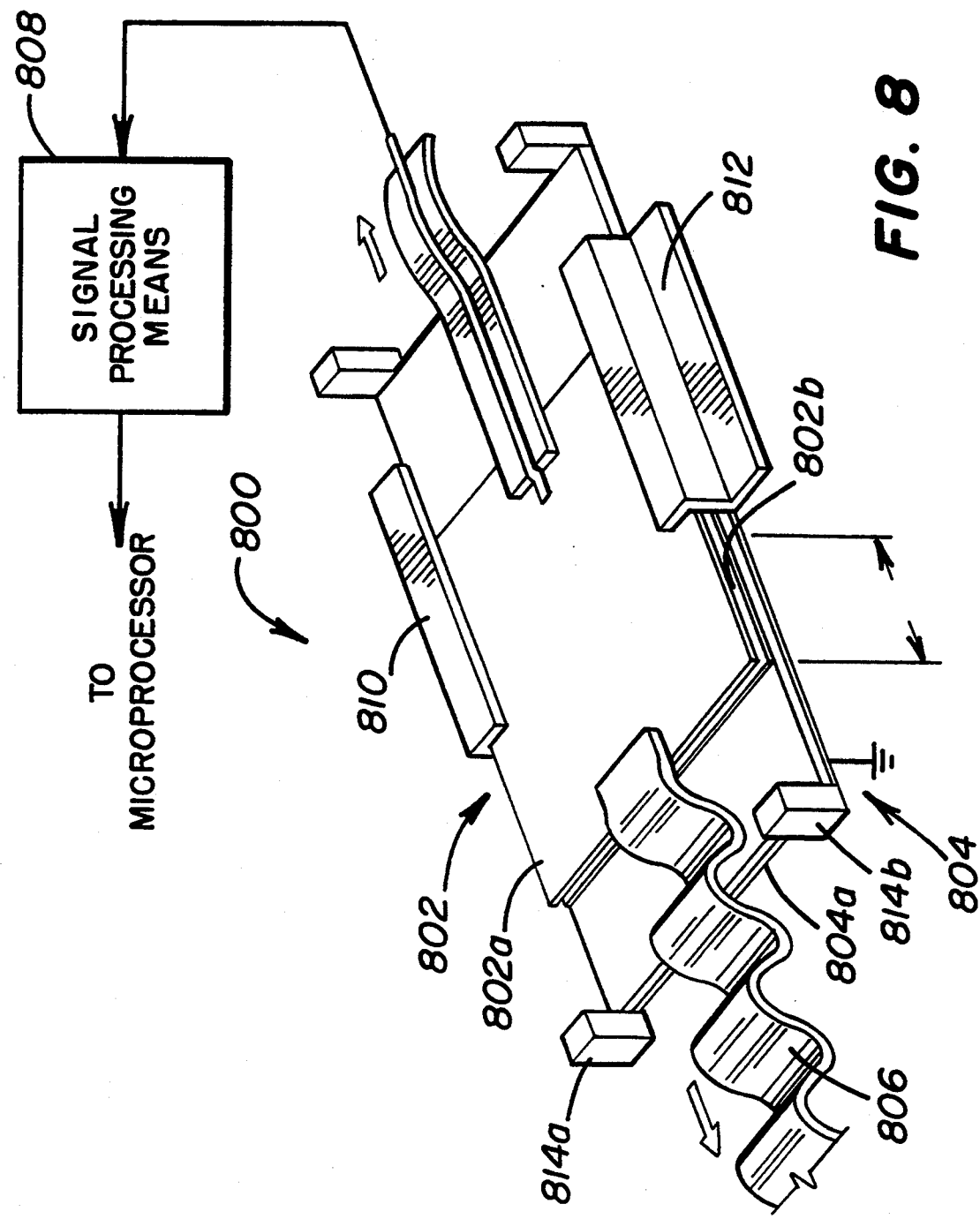
FIG. 8 is a perspective view of an apparatus for measuring the angular displacement of the SMA actuator elements to provide precise control of the SMA actuator film.

As shown in FIG. 8, a capacitive linear strain gauge 800 comprises two linearly overlapping composite plates 802, 804. Each composite plate 802, 804 comprises a thin film layer of conductive material 802a, 804a and a corresponding insulating layer 802b, 804b. The conductive layers can be sputtered, plated or otherwise deposited in accordance with well known VLSI processing techniques. The insulating layers 802b, 804b are adjacent one another and move laterally with respect to one another in response to linear displacement as indicated by the arrows in FIG. 8. One insulating layer 802b, for example, consists of SiNi. The adjacent insulating layer 804b is preferably teflon or the like. It is desirable to use composite layers 802, 804 with adjacently opposed insulating layers 802b, 804b in order to prevent breakdown, since the voltage in the SMA actuator film can be as high as $10^8$ volts per meter and the distance between conductive plates 802, 804 must be minimized.

Thus, the two conductive plates 802a, 804a are separated by an insulating medium, insulating layers 802b, 804b. The composite plates 802, 804 are disposed for linear motion in a single plane coincident with the plates 802, 804.

A return spring 806 of polyimide or other suitable material returns the plates 802, 804 to an initial rest position when the associated displacement force is removed. Captive elements 810, 812 are provided for constraining any out of plane motion. End stops 814a, 814b are provided for limiting the extent of linear travel.

In response to linear movement of an associated SMA actuator, the area of the overlapping plates 802, 804 decreases, thereby reducing the capacitance. The reduction of capacitance is sensed by signal processor 808 comprising local amplifying circuitry in accordance with signal processing techniques which are well known to those skilled in the art and which can be implemented without undue experimentation. What is important is that the capacitive linear strain gauges and associated signal processors are integrated in VLSI in the SMA actuator film. It is preferable to locate the signal processor means 808 as close as is practical to its associated capacitive linear strain gauge to prevent the weak signals from being lost in the noise. The function of the signal processor is to send amplified signals representative of the change in capacitance to the microprocessor.

In accordance with an aspect of the invention, the signal processor means 808 comprises a means for detecting phase and frequency of the weak signals from the capacitive linear strain gage 800. This is done preferably through a ring oscillator which is integrated in VLSI and incorporated in the SMA actuator film in accordance with known techniques. The ring oscillator compares a base frequency with a frequency which is altered by a change in capacitance. This provides the advantages of extreme sensitivity coupled with high immunity to noise. Thus, the signal processing means 808 is both extremely robust and able to withstand harsh operating environments while retaining extreme sensitivity. Accordingly this provides great precision in control of the SMA actuator film 100.

It has been found that there is a direct linear relationship between the linear displacement of the plates 802, 804 of the capacitive linear strain gauge 800 and the resultant capacitance. Thus, it is a simple process for the microprocessor to infer the position of each SMA actuator as a function of the detected change in capacitance. The capacitive linear strain gauge provides a means for measuring the joint angle of each of the SMA actuators with appropriate mechanical amplification in accordance with well known techniques. From this, the overall configuration of the SMA actuator film can be calculated for a given position.

The capacitive linear strain gauge described above has an advantage over conventional sensor means in that it can be downsized to very small dimensions and incorporated on the VLSI polyimide sheet 100 over or adjacent an associated SMA actuator 105. The coloration of sensors and SMA actuators provided by this aspect of the invention greatly improves controllability. The capacitive linear strain gage 800 also can detect extremely small amounts of displacement with extreme precision. This enables the movement of the SMA actuator film to be closely controlled by the microprocessor.

It will be appreciated that any number of other sensors adapted for VLSI fabrication may be incorporated in the SMA actuator film without departing from the scope of the present invention. For example, many types of sensor means for measuring parameters in the environment through which the SMA actuator film is moved may be integrally formed in VLSI on the SMA actuator film 100.

Hall effect sensors, fabricated in VLSI by known techniques, may be integrated in the SMA actuator film 100 for measuring magnetic fields. In surgical applications it is also advantageous to integrate VLSI sensor means for detecting changes in temperature or for detecting changes in chemical potential, such as an oxygen concentration sensor or the like in VLSI on the SMA actuator film for measuring minute changes in chemical concentration or changes in temperature.

One aspect of the present invention also contemplates the incorporation of a VLSI telemetry means at each SMA joint in the SMA actuator film for transmitting measurements made by the foregoing VLSI sensors to a remote receiver. For example, an ultrasonic transducer, electromagnetic transducer, microwave transducer or an LED transmitter/receiver pair could be integrated in VLSI on the SMA actuator film to provide instantaneous feedback of environmental parameters.

In medical applications, it would be advantageous to provide ultrasonic transducers integrated in VLSI at each joint in the SMA actuator film. The ultrasonic transducers could be used in combination with the telemetry means for imaging the position of the SMA actuator film and/or the intervening tissue or material surrounding the SMA actuator film.

Referring again to FIG. 6, in accordance with another aspect of the invention, it will be appreciated that a reference array established by the position mapping means 415 corresponds to a locus of angular positions which define an ideal axis of travel for the probe 400 as it is advanced along a path, no matter how geometrically complex. The reference array of the position mapping means 415 also corresponds to the angular position of each of the SMA actuator elements in a respective segment of the actuator film 100 for positional intervals on a path of travel. Thus, the configuration of the entire movable portion of the probe 400 can be derived by the microprocessor for any given point along the travel path.

In accordance with a further aspect of the invention, the position mapping means enables the probe 400 to spontaneously reverse its direction at any point along the path of travel. The data stored in the reference array of the position mapping means 415 enable the probe to precisely repeat the ideal path of travel in a reverse direction.

A probe or medical device such as a catheter, encased by the spatially distributed actuator film according to the present invention would be able to maneuver with unrestricted motion in three dimensions along a geometrically convoluted path while recording an ideal path of travel. Once a reference array establishing a locus of positions for defining an ideal axis of travel is established, the memorized path is repeatable with extreme speed and the probe or catheter can instantly reverse both its direction and the activation sequence determining its configuration so that it precisely retraces its positions for a complex path of travel. In this sense, a probe or catheter encased by the spatially distributed SMA actuator film of the present invention is self-guiding with respect to even the most complex path of travel which is stored in the position mapping means.

A steerable catheter encased by the SMA actuator film has significant advantages over conventional SMA steerable devices. For example, according to the present invention, a steerable catheter is controlled electronically, and is capable of sophisticated movements, such as stationary waves, automatic steering, and can be manipulated into a plurality of desired catheter end configurations. A device according to the present invention also could be fitted with ablation devices.

Further, the SMA steerable device according to the present invention can be articulated at $\frac{1}{2}$ second intervals and thereby can maintain compliant, non injurious contact with the surface of a heart muscle, even if the heart should undergo fibrillation. Since a catheter according to the present invention is extremely compliant until electrically activated, it will not damage vascular walls with excessive force when operated in an open loop mode.

While a basic application for the spatially distributed SMA actuator film of the present invention is in the field of medical devices, and particularly catheters, the present invention is not limited to use with a catheter device. A spatially distributed SMA actuator film with integral VLSI control and driver circuitry may be applied encase an active surgical tool, or a probe for nondestructive inspection, or any device wherein it is advantageous to provide unrestricted, remotely controlled motion in three-dimensional space.

For example, a spatially distributed SMA film in accordance with the present invention may be fitted with an active surgical element on its distal end. This could have broad applications in the field of robotic surgery since the surgical element can be self-guided along a path of travel in three dimensions when the locus of positions defining the ideal axis of travel is stored in the position mapping means.

A device according to the present invention also could be fitted with a miniature, silicon-based charge coupled device (CCD). This would enable one to optically image geometrically complex regions such as turbine engines or the like for defects. Since the present SMA actuator film can be downsized to a thickness of only a few microns, and is capable of being self-guided on a fixed path of travel, the present invention has broad application in medical devices, in the field of robotics, and particularly in the area of nondestructive testing. It will be appreciated that the foregoing aspects of the invention eliminate entirely the need for oppositely disposed actuator elements, external control arms, linkages, or the like which are necessary in conventional SMA steerable devices in order to return the SMA actuator elements to their original position after activation.

It will be appreciated that equivalent arrangements for centering the SMA actuator probe on a path of travel include a plurality of temperature sensors or proximity sensors which could be incorporated on the exterior on the probe and provide output signals which could be used to make a temperature gradient map or the like. Also, precise control of the probe can be achieved by measuring position, displacement (changes in position) and relative elongation of SMA actuators through linear variable differential transformers (LVDTs) or strain gauges. Such equivalent arrangements can be used with known adaptive feedback methods to center the probe on a path of travel and can be implemented by one skilled in the art without undue experimentation. Therefore, all such equivalent arrangements are intended to be within the scope of the appended claims.

Those of ordinary skill in the field will understand that SMA actuator elements may be comprised of any suitable one-way shape memory material such as Cu—Zn—Al, or TiNi, or the like. Additionally, those having ordinary skill in the field will appreciate that the SMA actuator elements may be configured in a variety of suitable shapes for maximizing the amount of useful movement derived from the change of phase from martensite to austenite as will be explained. Therefore, persons of ordinary skill in the art are to understand that all such equivalent structures and arrangements are to be included within the spirit and scope of the appended claims.

A shape memory alloy actuator as used herein includes any equivalent material that expands or contracts as a function of heating or cooling, or the application of an electric/magnetic field, such as shape memory metal actuators, a piezo-electric material, negative or positive coefficient of expansion material, or the like. Therefore, all such materials providing an equivalent function are intended to be within the scope of the appended claims.

What is claimed is:

1. A shape memory actuator film comprising:
   a flexible thin film base;
   a plurality of shape memory actuator means, provided on said, base adapted to impart movement to an adjacent portion of said base by deflection when resistively heated by an electric current of a predetermined value;
   switch means connected with a corresponding one of said shape memory actuator means, for applying said electric current to selectively activate one or more shape memory actuator means in response to control signals;
   control circuit means, for producing said control signals for selectively activating said switch means to produce desired three-dimensional movement of said base; wherein said base comprises a flexible thin film sheet comprising control and address decode circuitry integrated in VGSI over a portion of said sheet and a plurality of shape memory actuator means, operatively connected with said control and address decode circuitry, spatially distributed over a remaining portion of said flexible sheet for providing substantially continuous multi-node manipulation in three dimensions.

2. An apparatus according to claim 1 wherein said switch means comprise a plurality of CMOS transistors, each having an input lead connected to a voltage source, an enable lead connected with said control circuit means and an output lead for applying a predetermined phase activation current to a corresponding shape memory alloy actuator means.

3. An apparatus according to claim 1 wherein said base further comprises a series of corrugations, disposed for accommodating movement of said shape memory actuator means while limiting strain to a predetermined amount.

4. An apparatus according to claim 1 where said control circuit means comprises an address decode circuit responsive to a microprocessor means for selectively activating said switch means to effect desired movement of said substrate.

5. An apparatus according to claim 4 wherein said control means further comprises position mapping means for storing an activation sequence record comprising locus of angular positions of said shape memory alloy actuator means.

6. An apparatus according to claim 5 further comprising a plurality of sensor means disposed on said base in proximity to said actuator means for sensing the deflection of an associated segment of said base and for providing output signals representative thereof to said microprocessor.

7. An apparatus according to claim 6 wherein said microprocessor further comprises adaptive feedback means, responsive to said output signals from said sensor means for centering said substrate along a desired path of travel.

8. An apparatus according to claim 7 wherein said microprocessor further comprises means for producing output signals to said switch means for selectively activating said shape memory actuator means in a reverse sequence to enable said substrate to reverse its direction and corresponding configuration for any point along said path of travel.

9. A spatially distributed shape memory actuator film comprising:
   a flexible sheet
   a plurality of shape memory actuators provided at regularly spaced intervals over said sheet;
   a plurality of activation means, each connected to a corresponding one of said shape memory actuators, and responsive to control signals, for applying an electric current to resistively heat a selected shape memory actuator to its activation threshold for inducing deflection of said actuator;
   control means for producing said control signals to selected activation means such that when said sheet is configured to form a three-dimensional surface, such as a cylinder, said control signals produce coordinated movement of said sheet along a desired path of travel.

10. An apparatus according to claim 9 wherein said plurality of shape memory alloy actuators further comprise:
    an interleaved array of shape memory actuator elements deposited over a portion of said substrate such that when said substrate is configured as a cylinder, said actuator elements are spatially distributed over the surface of said cylinder, for imparting unrestricted three-dimensional movement thereto upon activation.

11. An apparatus according to claim 10 wherein said base further comprises a plurality of corrugation means extending substantially transversely to the axis of the cylinder for providing substantially continuous multijointed manipulation in three dimensions and limiting strain of said substrate to a predetermined amount.

12. A method for moving a probe with coordinated movement in three dimensions comprising:
    providing a plurality of shape memory actuators on a flexible sheet;
    fabricating in VLSI on said sheet a corresponding plurality of driver means for applying an electric current for resistively heating a corresponding shape memory actuator to an activation threshold;
    configuring said sheet in a three-dimensional configuration such as a cylinder, such that said shape memory actuators are positioned at intervals over the surface;
    providing a microprocessor having an electrical connection with said driver means for selectively enabling said driver means to activate selected shape memory actuators to produce desired movement along a path of travel.

13. A method according to claim 12 wherein said step of providing a plurality of shape memory actuators further includes the step of etching a series of corrugations in said sheet, said corrugations substantially transversely to a desired direction of motion of said shape memory actuators, to accommodate movement of said shape memory actuators.

14. A method according to claim 12 wherein said step of providing a plurality of shape memory actuators further includes the step of providing said shape memory actuators in an interleaved array on a flexible polyamide sheet and wrapping said sheet about a centrally disposed axis such that said shape memory actuators are spatially distributed around the circumference of said flexible sheet to provide coordinated motion without restriction in three-dimensional space.

15. A method for using a shape memory material for providing controlled movement in three dimensions comprising the steps of:
   providing a plurality of shape memory elements over a portion of a flexible sheet suitable for VLSI formation;
   providing a plurality of switch means, each connecting to a corresponding one of said shape memory elements for applying an electric current to resistively heat one or more selected shape memory elements to an activation threshold to thereby impart movement to said one or more selected shape memory elements;
   providing a control circuit means on a remaining portion of said sheet for connection to said switch means for selectively enabling said switch means to produce coordinated three-dimensional movement of said sheet in response to control signals.

16. A method according to claim 15 further comprising the steps of:
   providing a series of corrugations in said sheet disposed substantially transversely to a direction of motion produced by said shape memory elements;
   configuring said flexible sheet to form a three-dimensional surface with said corrugations disposed about the surface thereof and adapted to allow unrestricted motion in three-dimensional space upon coordinated activation of said shape memory alloy elements while limiting strain to a predetermined amount.

17. A method according to 15 wherein said step of providing a plurality of shape memory elements includes the step of providing said shape memory elements in an interleaved array such that when said sheet is configured as a three-dimensional surface such as a flexible tube, said shape memory elements are spatially distributed over the surface of said sheet for providing substantially continuous, coordinated movement of said sheet in three dimensions.

18. A method according to claim 16 wherein said step of configuring said sheet further comprises the step of wrapping said sheet around a hollow catheter tube to form a steerable catheter with coordinated motion in three dimensions.

19. A method according to claim 16 wherein said step of configuring said sheet further comprises the steps of:
   fitting an active surgical element on an end portion of said sheet; and
   selectively activating said shape memory elements for controllably moving said active surgical element to perform a desired surgical procedure.

20. A method according to claim 16 wherein said step of configuring said sheet further comprises the step of wrapping said sheet around a bendable element to impart desired motion in three-dimensional space to said bendable element upon activation of said shape memory elements.

21. A method of making a spatially distributed shape memory alloy actuator film for providing unrestricted movement in three-dimensional space comprising the steps of:
   providing a semiconductor substrate;
   forming a plurality of corrugations across said substrate;
   depositing an insulating layer over said substrate;
   sputtering a shape memory material such as TiNi or the like over said insulating layer;
   annealing said shape memory material;
   etching said annealed shape memory material to form discrete shape memory actuators;
   masking said shape memory actuator elements to form windows around each of said memory shape actuators;
   depositing a layer of a flexible, insulating material such as polyimide or the like over said plurality of shape memory alloy actuators;
   fabricating on said polyimide layer a plurality of VLSI switch means and associated address decode circuitry for connection to a corresponding one of each of said plurality of shape memory alloy actuators;
   releasing said polyimide layer from said substrate such that said shape memory alloy actuators, associated switch means and address decode and circuitry are integrated in VLSI on a single, flexible sheet;
   providing a microprocessor operatively connected with said address decode circuitry and switch means for selectively activating said shape memory alloy actuators to impart desired movement.

22. A method according to claim 21 wherein said step of depositing a plurality of shape memory alloy actuators further comprises the steps of:
   depositing through VLSI techniques a plurality of sensor means in proximity with each shape memory alloy element for measuring the joint angle of activated shape memory alloy actuators to provide control feedback for moving the shape memory alloy actuators in a desired manner.

23. A spatially distributed shape memory alloy actuator film for providing unrestricted movement in three-dimensional space comprising:
   a flexible thin film base;
   a plurality of shape memory actuator means provided on said base, each for producing deflection upon being resistively heated to a phase activation threshold by application of an electric current;
   a plurality of switch means provided on said base, each switch means having a connection with a corresponding one of said actuator means for resistively heating a corresponding actuator means upon receipt of a control signal;
   control means comprising address decode circuitry provided on said base for producing control signals to selected switch means, said control signals being representative of a desired deflection of a selected actuator means such that coordinated activation of selected actuator means imparts desired three-dimensional movement.

24. An apparatus according to claim 23 wherein said control means comprises adaptive feedback means further comprising a plurality of sensor means, each sensor means disposed for measuring angular position of a corresponding actuator means and connected in a feedback loop with said control means.

25. An apparatus according to claim 24 wherein said adaptive feedback means further comprises a plurality of capacitive linear strain gauge means, each disposed in close proximity to a corresponding actuator means for measuring a joint angle of a selected actuator means and for producing a measurable change in capacitance which is directly proportional to displacement of said actuator means.

26. An apparatus according claim 25 wherein said capacitive linear strain gauge means comprises two overlapping composite plates, each comprising a layer of sputtered conductive material over an insulating base, wherein the bases of said composite layers are disposed in adjacent sliding relation with respect to one another such that the movement of a corresponding actuator causes a linear displacement of said overlapping plates and produces a change in capacitance which is directly proportional to the displacement of said actuator means.

27. A shape memory actuator film comprising:
a flexible base;
a plurality of shape memory actuator means, deposited on said base, adapted to impart movement to an adjacent portion of said base by deflection when resistively heated by an electric current of a predetermined value;
switch means connected with a corresponding one of said shape memory actuator means, for applying said electric current to selectively activate one or more shape memory actuator means in response to control signals;
control circuit means for producing said control signals for selectively activating said switch means to produce desired three-dimensional movement of said base; and
wherein said base comprises a flexible, thin film sheet comprising control and address decode circuitry integrated in VLSI over a portion of said sheet and a plurality of shape memory actuator means, operatively connected with said control and address decode circuitry, spatially distributed over a remaining portion of said flexible sheet for providing substantially continuous multinode manipulation in three dimensions.

28. A method for moving a probe with coordinated movement in three dimensions comprising:
providing a plurality of shape memory actuators on a flexible sheet;
fabricating in VLSI on said sheet a corresponding plurality of driver means for applying an electric current for resistively heating a corresponding shape memory actuator to an activation threshold;
configuring said sheet in a three-dimensional configuration such as a cylinder, such that said shape memory actuators are positioned at intervals over the surface;
providing a microprocessor having an electrical connection with said driver means for selectively enabling said driver means to activate selected shape memory actuators to produce desired movement along a path of travel; and
providing a series of corrugations in said sheet, said corrugations extending substantially transversely to a desired direction of motion of said shape memory actuators to accommodate movement of said shape memory actuators.

29. A method for moving a probe with coordinated movement in three dimensions comprising:
providing a plurality of shape memory actuators on a flexible sheet;
fabricating in VLSI on said sheet a corresponding plurality of driver means for applying an electric current for resistively heating a corresponding shape memory actuator to an activation threshold;
configuring said sheet in a three-dimensional configuration such as a cylinder, such that said shape memory actuators are positioned at intervals over the surface;
providing a microprocessor having an electrical connection with said driver means for selectively enabling said driver means to activate selected shape memory actuators to produce desired movement along a path of travel;
providing a series of corrugations in said sheet, said corrugations extending substantially transversely to a desired direction of motion of said shape memory actuators to accommodate movement of said shape memory actuators; and
wherein said step of providing a plurality of shape memory actuators further includes the step of providing said shape memory actuators in an interleaved array on a flexible polyamide sheet and wrapping said sheet about a centrally disposed axis such that said shape memory actuators are spatially distributed around the circumference of said sheet to provide coordinated motion without restriction in three-dimensional space.

30. A method for using a shape memory material for providing controlled movement in three dimensions comprising the steps of:
providing a plurality of shape memory elements over a portion of a flexible sheet suitable for VLSI formation;
providing a plurality of switch means, each connecting to a corresponding one of said shape memory elements for applying an electric current to resistively heat one or more said shape memory elements to an activation threshold to thereby impart movement to said one or more selected shape memory elements;
providing a control circuit means on a remaining portion of said sheet for connection to said switch means for selectively enabling said switch means to produce coordinated three-dimensional movement of said sheet in response to control signals;
providing a series of corrugations in said sheet disposed substantially transversely to a direction of motion produced by shape memory elements;
configuring said flexible sheet to form a three-dimensional surface with said corrugations disposed about the surface thereof and adapted to allow unrestricted motion in three-dimensional space upon coordinated activation of said shape memory alloy elements while limiting strain to a predetermined amount; and
wherein said step of providing a plurality of shape memory elements includes the step of providing a plurality of shape memory elements in an interleaved array such that when said sheet is configured as a three-dimensional surface such as a flexible tube, said shape memory elements are spatially distributed over the surface of said sheet for providing substantially continuous, coordinated movement of said sheet in three dimensions.

31. A method according to claim 30 wherein said step of configuring said sheet further comprises the step of wrapping said sheet around a hollow catheter tube to form a steerable catheter with coordinated motion in three dimensions.

32. A method according to claim 30 wherein the step of configuring the sheet further comprises the steps of:
fitting an active surgical element on an end portion of said sheet; and
selectively activating said shape memory elements for controllably moving said active surgical element to perform a desired surgical procedure.

33. A method according to claim 30 wherein said of configuring said sheet further comprises the step of wrapping said sheet around a bendable element to impart desired motion in three-dimensional space to said bendable element upon activation of said shape memory elements.

34. A spatially distributed shape memory alloy actuator film for providing unrestricted movement in three-dimensional space comprising:
a flexible thin film base;
a plurality of shape memory actuator means provided on said base, each for producing deflection upon being resistively heated to a phase activation threshold by application of an electric current;
a plurality of switch means provided on said base, each switch means having a connection with a corresponding one of said actuator means for resistively heating a corresponding actuator means upon receipt of a control signal;
control means comprising address decode circuitry provided on said base for producing said control signals to selected switch means, said control signals being representative of a desired deflection of a selected actuator means such that coordinated activation of selected actuator means imparts desired three-dimensional movement; and
wherein said control means further comprises adaptive feedback means comprising a plurality of sensor means, each sensor means disposed for measuring angular position of a actuator means and connected in a feedback loop with said control means.

35. An apparatus according to claim 34 wherein said adaptive feedback means further comprises a plurality of capacitative linear strain gauge means, each disposed in close proximity to a corresponding actuator means for measuring a joint angle of a selected actuator means and for producing a measurable change in capacitance which is directly proportional to displacement of said actuator means.

36. An apparatus according to claim 35 wherein said capacitive linear strain gauge means comprises two overlapping composite plates, each comprising a layer of sputtered conductive material over an insulating base, wherein the basis of said composite layers are disposed in adjacent sliding relation with respect to one another such that the movement of a corresponding actuator causes a linear displacement of said overlapping plates and produces a change in capacitance which is directly proportional to the displacement of said actuator means.

* * * * *